United States Patent
Kopecek et al.

(10) Patent No.: US 10,925,973 B2
(45) Date of Patent: Feb. 23, 2021

(54) COMPOSITIONS AND METHODS FOR USING ALBUMIN-BASED NANOMEDICINES

(71) Applicant: University of Utah Research Foundation, Salt Lake City, UT (US)

(72) Inventors: Jindrich Henry Kopecek, Salt Lake City, UT (US); Jiyuan Yang, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

(21) Appl. No.: 16/310,754

(22) PCT Filed: Jun. 15, 2017

(86) PCT No.: PCT/US2017/037736
§ 371 (c)(1),
(2) Date: Dec. 17, 2018

(87) PCT Pub. No.: WO2017/218813
PCT Pub. Date: Dec. 21, 2017

(65) Prior Publication Data
US 2019/0175751 A1  Jun. 13, 2019

Related U.S. Application Data

(60) Provisional application No. 62/350,462, filed on Jun. 15, 2016.

(51) Int. Cl.
| | | |
|---|---|---|
| *C12N 15/113* | (2010.01) | |
| *A61K 47/68* | (2017.01) | |
| *A61K 47/64* | (2017.01) | |
| *C07K 16/28* | (2006.01) | |
| *A61K 31/712* | (2006.01) | |

(52) U.S. Cl.
CPC ........ *A61K 47/6897* (2017.08); *A61K 31/712* (2013.01); *A61K 47/643* (2017.08); *A61K 47/6807* (2017.08); *A61K 47/6849* (2017.08); *A61K 47/6867* (2017.08); *C07K 16/2887* (2013.01); *C07K 2317/55* (2013.01); *C07K 2317/73* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,217,866 A | 6/1993 | Summerton et al. |
| 5,476,766 A | 12/1995 | Gold et al. |
| 5,503,978 A | 4/1996 | Schneider et al. |
| 5,506,337 A | 4/1996 | Summerton et al. |
| 5,521,063 A | 5/1996 | Summerton et al. |
| 5,631,146 A | 5/1997 | Szostak et al. |
| 5,698,685 A | 12/1997 | Summerton et al. |
| 5,731,424 A | 3/1998 | Toothman et al. |
| 5,780,228 A | 7/1998 | Parma et al. |
| 5,792,613 A | 8/1998 | Schmidt et al. |
| 5,795,721 A | 8/1998 | Rabin et al. |
| 5,846,713 A | 12/1998 | Pagratis et al. |
| 5,858,660 A | 1/1999 | Eaton et al. |
| 5,861,254 A | 1/1999 | Schneider et al. |
| 5,864,026 A | 1/1999 | Jensen et al. |
| 5,869,641 A | 2/1999 | Jayasena et al. |
| 5,958,691 A | 9/1999 | Pieken et al. |
| 6,001,988 A | 12/1999 | Parma et al. |
| 6,011,020 A | 1/2000 | Gold et al. |
| 6,013,443 A | 1/2000 | Heilig et al. |
| 6,020,130 A | 2/2000 | Gold et al. |
| 6,028,186 A | 2/2000 | Tasset et al. |
| 6,030,776 A | 2/2000 | Eaton et al. |
| 6,051,698 A | 4/2000 | Janjic et al. |
| 2007/0010014 A1 | 1/2007 | Wood et al. |
| 2016/0015732 A1 | 1/2016 | Kopeček et al. |

FOREIGN PATENT DOCUMENTS

| | | |
|---|---|---|
| EP | 2556087 A1 | 2/2013 |
| EP | 17814117.2 | 1/2019 |
| WO | WO-2011/124718 A1 | 10/2011 |
| WO | WO-2014/164913 A1 | 10/2014 |
| WO | PCT/US2017/218813 | 6/2017 |

OTHER PUBLICATIONS

Wu et al. "Coiled-coil based drug-free macromolecular therapeutics: In vivo efficacy", Journal of Controlled Release 157 (2012) 126-131 available online Aug. 6, 2011.*
Andersen, J.T. et al., Extending serum half-life of albumin by engineering neonatal Fc receptor (FcRn) binding. J Biol Chem. 2014; 289(19):13492-502.
Anderson, K.C. et al., Expression of human B cell-associated antigens on leukemias and lymphomas: a model of human B cell differentiation. Blood. 1984; 63(6):1424-33.
Armitage, J.O. and Weisenburger, D.D. New approach to classifying non-Hodgkin's lymphomas: clinical features of the major histologic subtypes. Non-Hodgkin's lymphoma classification project. J Clin Oncol. 1998; 16(8):2780-95.
Bern, M. et al., The role of albumin receptors in regulation of albumin homeostasis: Implications for drug delivery. J Control Release. 2015; 211:144-62.

(Continued)

*Primary Examiner* — Kimberly Chong
(74) *Attorney, Agent, or Firm* — Ballard Spahr LLP

(57) ABSTRACT

In an aspect, the invention relates to compositions, methods, and kits for inducing apoptosis. This abstract is intended as a scanning tool for purposes of searching in the particular art and is not intended to be limiting of the present invention.

16 Claims, 8 Drawing Sheets
Specification includes a Sequence Listing.

(56) References Cited

OTHER PUBLICATIONS

Boross, P. and Leusen, J.H.W., Mechanisms of action of CD20 antibodies. Am J Res. 2012; 2(6):676-90.

Bubien, J.K. et al., Transfection of the CD20 cell surface molecule into ectopic cell types generates a Ca2+ conductance found constitutively in B lymphocytes. J Cell Biol. 1993; 121(5):1121-32.

Cartron, G. et al., Therapeutic activity of humanized anti-CD20 monoclonal antibody and polymorphism in IgG Fc receptor Fc?RIIIa gene. Blood. 2002; 99(3):754-8.

Cheson, B.D. and Leonard, J.P., Monoclonal antibody therapy for B-cell non-Hodgkin's lymphoma. N Engl J Med. 2008; 359:613-26.

Chu, T.-W. and Kopeček, J., Drug-free macromolecular therapeutics—a new paradigm in polymeric nanomedicines. Biomater Sci. 2015; 3(7):908-22 (27 pages).

Chu, T.-W. et al., A two-step pretargeted nanotherapy for CD20 crosslinking may achieve superior anti-lymphoma efficacy to rituximab. Theranostics. 2015; 5(8):834-46.

Chu, T.-W. et al., Cell surface self-assembly of hybrid nanoconjugates via oligonucleotide hybridization induces apoptosis. ACS Nano. 2014; 8(1):719-30 (25 pages).

Chu, T.-W. et al., Drug-free macromolecular therapeutics induce apoptosis of patient chronic lymphocytic leukemia cells. Drug Deliv Transl Res. 2014; 4(5-6):389-94.

Desai, N. et al., SPARC expression correlates with tumor response to albumin-bound paclitaxel in head and neck cancer patients. Transl Oncol. 2009; 2(2):59-64.

Dransfield, I., Inhibitory Fc?RIIb and CD20 internalization. Blood. 2014; 123(5):606-7.

Elsadek, B. and Katz, F., Impact of albumin on drug delivery—New applications on the horizon. J Control Release. 2012; 157(1):4-28.

Ghetie, A.M. et al., The Antitumor activity of an anti-CD22 immunotoxin in SCID mice with disseminated Daudi lymphoma is enhanced by either an anti-CD19 antibody or an anti-CD19 immunotoxin. Blood. 1992; 80(9):2315-20.

Ghetie, M.A. et al., Disseminated or localized growth of a human B-cell tumor (Daudi) in SCID mice. Int J Cancer. 1990; 45(3):481-5.

Griffiths, G.L. et al., Cure of SCID mice bearing human B-lymphoma xenografts by an anti-CD74 antibody-anthracycline drug conjugate. Clin Cancer Res. 2003; 9(17):6567-71.

Gunn, J. et al., A pretargeted nanoparticle system for tumor cell labeling. Mol Biosyst. 2011; 7(3):742-8.

Hartley, J.M. et al., Super-resolution imaging and quatitative analysis of membrane protein/lipid raft clustering mediated by cell surface self-assembly of hybrid nanoconjugates. ChemBioChem. 2015; 16(12):1725-9 (12 pages).

Janas, E. et al., Functional role of lipid rafts in CD20 activity? Biochem Soc Symp. 2005; 72:165-75.

Kratz, F., Albumin as a drug carrier: Design of prodrugs, drug conjugates and nanoparticles. J Control Release. 2008; 132(3):171-83.

Liu, G. et al., Pretargeting in tumored mice with radiolabeled morpholino oligomer showing low kidney uptake. Eur J Nucl Med Mol Imaging. 2004; 31(3):417-24.

Liu, G. et al., Successful radiotherapy of tumor in pretargeted mice by 188Re-radiolabeled phosphorodiamidate morpholino oligomer, a synthetic DNA analogue. Clin Cancer Res. 2006; 12(16):4958-64 (16 pages).

Maloney, D.G. et al., IDEC-C2B8 (Rituximab) anti-CD20 monoclonal antibody therapy in patients with relapsed low-grade non-Hodgkin's lymphoma. Blood. 1997; 90(6):2188-95.

Maloney, D.G., Anti-CD20 antibody therapy for B-cell lymphomas. N Engl J Med. 2012; 366:2008-16.

Michel, R.B. And Mattes, M.J., Intracellular accumulation of the anti-CD20 antibody 1F5 in B-lymphoma cells. Clin Cancer Res. 2002; 8(8):2701-13.

Molina, A., A decade of rituximab: improving survival outcomes in non-Hodgkin's lymphoma. Annu Rev Med. 2008; 59:237-50.

Mulvey, J.J. et al., Self-assembly of carbon nanotubes and antibodies on tumours for targeted, amplified delivery. Nat Nanotechnol. 2013; 8:763-71.

Okroj, M. et al., Effector mechanisms of anti-CD20 monoclonal antibodies in B cell malignancies. Cancer Treat Rev. 2013; 39(6):632-9.

Pham, T. et al., Dynamics of macrophage trogocytosis of rituximab-coated B cells. PloS One. 2011; 6:e14498 (11 pages).

Press, O.W. et al., Endocytosis and degradation of monoclonal antibodies targeting human B-cell malignancies. Cancer Res. 1989; 49(17):4906-12.

Qi, W.-W. et al., Doxorubicin-Loaded Glycyrrhetinic Acid Modified Recombinant Human Serum Albumin Nanoparticles for Targeting Liver Tumor Chemotherapy. Mol Pharma. 2015; 12:675-83.

Sethi, A. et al., Albumin as a drug delivery and diagnostic tool and its market approved products. Acta Pol Pharma-Drug Res. 2013; 70(4):597-600.

Shan, D. et al., Apoptosis of malignant human B cells by ligation of CD20 with monoclonal antibodies. Blood. 1998; 91(5):1644-52.

Shankland, K.R. et al., Non-Hodgkin lymphoma. Lancet. 2012; 380(9844):848-57.

Siegel, R.L. et al., Cancer statistics, 2015. CA Cancer J Clin. 2015; 65(1):5-29.

Smith, M.R., Rituximab (monoclonal anti-CD20 antibody): mechanisms of action and resistance. Oncogene. 2003; 22(47):7359 (10 pages).

Stashenko, P. et al., Characterization of a human B lymphocyte-specific antigen. J Immunol. 1980; 125(4):1678-85.

Tedder, T.F. and Engel, P., CD20: a regulator of cell-cycle progression of B lymphocytes. Immunol Today. 1994; 15(9):450-4 (3 pages).

Wu, K. et al., Drug-free macromolecular therapeutics: Induction of apoptosis by coiled-coil mediated crosslinking of antigens on cell surface. Angew Chem Int Ed Engl. 2010; 49(8):1451-5 (10 pages).

Zelenetz, A.D. et al., Non-Hodgkin's lymphomas, version 4.2014. J Natl Compr Cancer Netw. 2014; 12(9):1282-303.

Zhang, R. et al., Multimodality imaging of coiled-coil mediated self-assembly in a "drug-free" therapeutic system. Adv Healthc Mater. 2015; 4(7):1054-65 (21 pages).

International Search Report and Written Opinion dated Nov. 2, 2017 by the International Searching Authority for Patent Application No. PCT/US2017/037736, which was filed on Jun. 15, 2017 and published as WO 2017/218813 on Dec. 21, 2017 (Inventor—Kopecek et al.; Applicant—University of Utah Research Foundation; (16 pages).

International Preliminary Report on Patentability dated Dec. 18, 2018 by the International Searching Authority for Patent Application No. PCT/US2017/037736, which was filed on Jun. 15, 2017 and published as WO 2017/218813 on Dec. 21, 2017 (Inventor—Kopecek et al.; Applicant—University of Utah Research Foundation; (12 pages).

Ming Xin et al: "Albumin-based nanoconjugates for targeted delivery of therapeutic oligonucleotides",Biomaterials,vol. 34, No. 32, (2013), pp. 7939-7949.

European Search Report and Written Opinion were dated Jan. 30, 2020 by the European Patent Office for EP Application No. 17814117.2, filed on Jun. 15, 2017 and published as EP3471740 A1 on Apr. 24, 2019 (Applicant-Univ. of Utah Research Foundation) (9 pages).

U.S. Appl. No. 62/350,462, filed Jun. 15, 2016, Jindrich H. Kopeček (Univ. Utah Res. Found.).

\* cited by examiner

SEQUENCE LISTING

```
<160> NUMBER OF SEQ ID NOS: 83

<210> SEQ ID NO 1
<211> LENGTH: 25
<212> TYPE: DNA
<213> ORGANISM: Artificial Sequence
<220> FEATURE:
<223> OTHER INFORMATION: 99mTc-labeled MORFs

<400> SEQUENCE: 1
aaaaaaaaaa aaaaaaaaaa aaaaa                                              25

<210> SEQ ID NO 2
<211> LENGTH: 25
<212> TYPE: DNA
<213> ORGANISM: Artificial Sequence
<220> FEATURE:
<223> OTHER INFORMATION: 99mTc-labeled MORFs

<400> SEQUENCE: 2
tttttttttt tttttttttt ttttt                                              25

<210> SEQ ID NO 3
<211> LENGTH: 25
<212> TYPE: DNA
<213> ORGANISM: Artificial Sequence
<220> FEATURE:
<223> OTHER INFORMATION: 99mTc-labeled MORFs

<400> SEQUENCE: 3
aagaagaaga agaagaagaa gaaga                                              25

<210> SEQ ID NO 4
<211> LENGTH: 15
<212> TYPE: DNA
<213> ORGANISM: Artificial Sequence
<220> FEATURE:
<223> OTHER INFORMATION: 99mTc-labeled MORFs

<400> SEQUENCE: 4
```

```
tagttgtgac gtaca                                                     15

<210> SEQ ID NO 5
<211> LENGTH: 15
<212> TYPE: DNA
<213> ORGANISM: Artificial Sequence
<220> FEATURE:
<223> OTHER INFORMATION: 99mTc-labeled MORFs

<400> SEQUENCE: 5
atcaacactg cttgt                                                     15

<210> SEQ ID NO 6
<211> LENGTH: 18
<212> TYPE: DNA
<213> ORGANISM: Artificial Sequence
<220> FEATURE:
<223> OTHER INFORMATION: 99mTc-labeled MORFs

<400> SEQUENCE: 6
atcaacactg cttgtggg                                                  18

<210> SEQ ID NO 7
<211> LENGTH: 25
<212> TYPE: DNA
<213> ORGANISM: Artificial Sequence
<220> FEATURE:
<223> OTHER INFORMATION: 99mTc-labeled MORFs

<400> SEQUENCE: 7
atcaacactg cttgtgggtg gtggt                                          25

<210> SEQ ID NO 8
<211> LENGTH: 18
<212> TYPE: DNA
<213> ORGANISM: Artificial Sequence
<220> FEATURE:
<223> OTHER INFORMATION: 99mTc-labeled MORFs

<400> SEQUENCE: 8
tagttgtgac gtacaccc                                                  18

<210> SEQ ID NO 9
<211> LENGTH: 25
<212> TYPE: DNA
<213> ORGANISM: Artificial Sequence
<220> FEATURE:
<223> OTHER INFORMATION: 99mTc-labeled MORFs

<400> SEQUENCE: 9
tagttgtgac gtacacccac cacca                                          25

<210> SEQ ID NO 10
<211> LENGTH: 20
<212> TYPE: DNA
<213> ORGANISM: Artificial Sequence
<220> FEATURE:
<223> OTHER INFORMATION: 99mTc-labeled MORFs

<400> SEQUENCE: 10
caccaccccc ctcgctggtc                                                20

<210> SEQ ID NO 11
<211> LENGTH: 25
<212> TYPE: DNA
<213> ORGANISM: Artificial Sequence
```

-continued

```
<220> FEATURE:
<223> OTHER INFORMATION: 99mTc-labeled MORFs

<400> SEQUENCE: 11
cccccccccc cccccccccc ccccc                                          25

<210> SEQ ID NO 12
<211> LENGTH: 40
<212> TYPE: DNA
<213> ORGANISM: Artificial Sequence
<220> FEATURE:
<223> OTHER INFORMATION: MORF1-a

<400> SEQUENCE: 12
gaactaatgc aataactatc acgaatgcgg gtaacttaat                          40

<210> SEQ ID NO 13
<211> LENGTH: 39
<212> TYPE: DNA
<213> ORGANISM: Artificial Sequence
<220> FEATURE:
<223> OTHER INFORMATION: MORF2-a

<400> SEQUENCE: 13
attaagttac ccgcattcgt gatagttatt gcattagtt                           39

<210> SEQ ID NO 14
<211> LENGTH: 40
<212> TYPE: DNA
<213> ORGANISM: Artificial Sequence
<220> FEATURE:
<223> OTHER INFORMATION: MORF1-b

<400> SEQUENCE: 14
gaaaccgcta tttattggct aagaacagat acgaatcata                          40

<210> SEQ ID NO 15
<211> LENGTH: 40
<212> TYPE: DNA
<213> ORGANISM: Artificial Sequence
<220> FEATURE:
<223> OTHER INFORMATION: MORF2-b

<400> SEQUENCE: 15
tatgattcgt atctgttctt agccaataaa tagcggtttc                          40

<210> SEQ ID NO 16
<211> LENGTH: 38
<212> TYPE: DNA
<213> ORGANISM: Artificial Sequence
<220> FEATURE:
<223> OTHER INFORMATION: MORF1-c

<400> SEQUENCE: 16
gtaaacgcga caaatgccga taatgcttcg ataataat                            38

<210> SEQ ID NO 17
<211> LENGTH: 38
<212> TYPE: DNA
<213> ORGANISM: Artificial Sequence
<220> FEATURE:
<223> OTHER INFORMATION: MORF2-c

<400> SEQUENCE: 17
attattatcg aagcattatc ggcatttgtc gcgtttac                            38
```

<210> SEQ ID NO 18
<211> LENGTH: 38
<212> TYPE: DNA
<213> ORGANISM: Artificial Sequence
<220> FEATURE:
<223> OTHER INFORMATION: MORF1-d

<400> SEQUENCE: 18
gacagagttc actatgacaa acgatttcac gagtaata                    38

<210> SEQ ID NO 19
<211> LENGTH: 38
<212> TYPE: DNA
<213> ORGANISM: Artificial Sequence
<220> FEATURE:
<223> OTHER INFORMATION: MORF2-d

<400> SEQUENCE: 19
tattactcgt gaaatcgttt gtcatagtga actctgtc                    38

<210> SEQ ID NO 20
<211> LENGTH: 35
<212> TYPE: DNA
<213> ORGANISM: Artificial Sequence
<220> FEATURE:
<223> OTHER INFORMATION: MORF1-e

<400> SEQUENCE: 20
cctgatacag aagtagaaag cagtcacgca atata                       35

<210> SEQ ID NO 21
<211> LENGTH: 35
<212> TYPE: DNA
<213> ORGANISM: Artificial Sequence
<220> FEATURE:
<223> OTHER INFORMATION: MORF2-e

<400> SEQUENCE: 21
tatattgcgt gactgctttc tacttctgta tcagg                       35

<210> SEQ ID NO 22
<211> LENGTH: 35
<212> TYPE: DNA
<213> ORGANISM: Artificial Sequence
<220> FEATURE:
<223> OTHER INFORMATION: MORF1-f

<400> SEQUENCE: 22
gaacaacgag aggtgctcaa tacagatatc aatca                       35

<210> SEQ ID NO 23
<211> LENGTH: 35
<212> TYPE: DNA
<213> ORGANISM: Artificial Sequence
<220> FEATURE:
<223> OTHER INFORMATION: MORF2-f

<400> SEQUENCE: 23
tgattgatat ctgtattgag cacctctcgt tgttc                       35

<210> SEQ ID NO 24
<211> LENGTH: 32
<212> TYPE: DNA
<213> ORGANISM: Artificial Sequence
<220> FEATURE:
<223> OTHER INFORMATION: MORF1-g

```
<400> SEQUENCE: 24
agtcatagat agacagaata gccggataaa ct                                    32

<210> SEQ ID NO 25
<211> LENGTH: 32
<212> TYPE: DNA
<213> ORGANISM: Artificial Sequence
<220> FEATURE:
<223> OTHER INFORMATION: MORF2-g

<400> SEQUENCE: 25
agtttatccg gctattctgt ctatctatga ct                                    32

<210> SEQ ID NO 26
<211> LENGTH: 32
<212> TYPE: DNA
<213> ORGANISM: Artificial Sequence
<220> FEATURE:
<223> OTHER INFORMATION: MORF1-h

<400> SEQUENCE: 26
gatacagaag tagaaagcag tcacgcaata ta                                    32

<210> SEQ ID NO 27
<211> LENGTH: 32
<212> TYPE: DNA
<213> ORGANISM: Artificial Sequence
<220> FEATURE:
<223> OTHER INFORMATION: MORF2-h

<400> SEQUENCE: 27
tatattgcgt gactgctttc tacttctgta tc                                    32

<210> SEQ ID NO 28
<211> LENGTH: 30
<212> TYPE: DNA
<213> ORGANISM: Artificial Sequence
<220> FEATURE:
<223> OTHER INFORMATION: MORF1-i

<400> SEQUENCE: 28
ggcatagata acagaatagc cggataaact                                       30

<210> SEQ ID NO 29
<211> LENGTH: 30
<212> TYPE: DNA
<213> ORGANISM: Artificial Sequence
<220> FEATURE:
<223> OTHER INFORMATION: MORF2-i

<400> SEQUENCE: 29
agtttatccg gctattctgt tatctatgcc                                       30

<210> SEQ ID NO 30
<211> LENGTH: 30
<212> TYPE: DNA
<213> ORGANISM: Artificial Sequence
<220> FEATURE:
<223> OTHER INFORMATION: MORF1-j

<400> SEQUENCE: 30
gaccagtaga taagtgaacc agattgaaca                                       30

<210> SEQ ID NO 31
```

<210> SEQ ID NO 31
<211> LENGTH: 30
<212> TYPE: DNA
<213> ORGANISM: Artificial Sequence
<220> FEATURE:
<223> OTHER INFORMATION: MORF2-j

<400> SEQUENCE: 31
tgttcaatct ggttcactta tctactggtc                                30

<210> SEQ ID NO 32
<211> LENGTH: 28
<212> TYPE: DNA
<213> ORGANISM: Artificial Sequence
<220> FEATURE:
<223> OTHER INFORMATION: MORF1-k

<400> SEQUENCE: 32
gagtacagcc agagagagaa tcaatata                                  28

<210> SEQ ID NO 33
<211> LENGTH: 28
<212> TYPE: DNA
<213> ORGANISM: Artificial Sequence
<220> FEATURE:
<223> OTHER INFORMATION: MORF2-k

<400> SEQUENCE: 33
tatattgatt ctctctctgg ctgtactc                                  28

<210> SEQ ID NO 34
<211> LENGTH: 28
<212> TYPE: DNA
<213> ORGANISM: Artificial Sequence
<220> FEATURE:
<223> OTHER INFORMATION: MORF1-l

<400> SEQUENCE: 34
gtgaacacga aagagtgacg caataaat                                  28

<210> SEQ ID NO 35
<211> LENGTH: 28
<212> TYPE: DNA
<213> ORGANISM: Artificial Sequence
<220> FEATURE:
<223> OTHER INFORMATION: MORF2-l

<400> SEQUENCE: 35
atttattgcg tcactctttc gtgttcac                                  28

<210> SEQ ID NO 36
<211> LENGTH: 25
<212> TYPE: DNA
<213> ORGANISM: Artificial Sequence
<220> FEATURE:
<223> OTHER INFORMATION: MORF1-m

<400> SEQUENCE: 36
gagtaagcca aggagaatca atata                                     25

<210> SEQ ID NO 37
<211> LENGTH: 25
<212> TYPE: DNA
<213> ORGANISM: Artificial Sequence
<220> FEATURE:
<223> OTHER INFORMATION: MORF2-m

<400> SEQUENCE: 37

```
tatattgatt ctccttggct tactc                                          25

<210> SEQ ID NO 38
<211> LENGTH: 25
<212> TYPE: DNA
<213> ORGANISM: Artificial Sequence
<220> FEATURE:
<223> OTHER INFORMATION: MORF1-n

<400> SEQUENCE: 38
agatgacgat aaagacgcaa agatt                                          25

<210> SEQ ID NO 39
<211> LENGTH: 25
<212> TYPE: DNA
<213> ORGANISM: Artificial Sequence
<220> FEATURE:
<223> OTHER INFORMATION: MORF2-n

<400> SEQUENCE: 39
aatctttgcg tctttatcgt catct                                          25

<210> SEQ ID NO 40
<211> LENGTH: 23
<212> TYPE: DNA
<213> ORGANISM: Artificial Sequence
<220> FEATURE:
<223> OTHER INFORMATION: MORF1-o

<400> SEQUENCE: 40
ggaccaagta aacagggata tat                                            23

<210> SEQ ID NO 41
<211> LENGTH: 23
<212> TYPE: DNA
<213> ORGANISM: Artificial Sequence
<220> FEATURE:
<223> OTHER INFORMATION: MORF2-o

<400> SEQUENCE: 41
atatatccct gtttacttgg tcc                                            23

<210> SEQ ID NO 42
<211> LENGTH: 23
<212> TYPE: DNA
<213> ORGANISM: Artificial Sequence
<220> FEATURE:
<223> OTHER INFORMATION: MORF1-p

<400> SEQUENCE: 42
gctgaaaacc aatatgagag tga                                            23

<210> SEQ ID NO 43
<211> LENGTH: 23
<212> TYPE: DNA
<213> ORGANISM: Artificial Sequence
<220> FEATURE:
<223> OTHER INFORMATION: MORF2-p

<400> SEQUENCE: 43
tcactctcat attggttttc agc                                            23

<210> SEQ ID NO 44
<211> LENGTH: 20
<212> TYPE: DNA
```

```
<213> ORGANISM: Artificial Sequence
<220> FEATURE:
<223> OTHER INFORMATION: MORF1-q

<400> SEQUENCE: 44
gatgaagtac cgacaagata                                                 20

<210> SEQ ID NO 45
<211> LENGTH: 20
<212> TYPE: DNA
<213> ORGANISM: Artificial Sequence
<220> FEATURE:
<223> OTHER INFORMATION: MORF2-q

<400> SEQUENCE: 45
tatcttgtcg gtacttcatc                                                 20

<210> SEQ ID NO 46
<211> LENGTH: 20
<212> TYPE: DNA
<213> ORGANISM: Artificial Sequence
<220> FEATURE:
<223> OTHER INFORMATION: MORF1-r

<400> SEQUENCE: 46
gacaggatga ataacacagt                                                 20

<210> SEQ ID NO 47
<211> LENGTH: 20
<212> TYPE: DNA
<213> ORGANISM: Artificial Sequence
<220> FEATURE:
<223> OTHER INFORMATION: MORF2-r

<400> SEQUENCE: 47
actgtgttat tcatcctgtc                                                 20

<210> SEQ ID NO 48
<211> LENGTH: 18
<212> TYPE: DNA
<213> ORGANISM: Artificial Sequence
<220> FEATURE:
<223> OTHER INFORMATION: MORF1-s

<400> SEQUENCE: 48
gcagcaaacg aagtatat                                                   18

<210> SEQ ID NO 49
<211> LENGTH: 18
<212> TYPE: DNA
<213> ORGANISM: Artificial Sequence
<220> FEATURE:
<223> OTHER INFORMATION: MORF2-s

<400> SEQUENCE: 49
atatacttcg tttgctgc                                                   18

<210> SEQ ID NO 50
<211> LENGTH: 18
<212> TYPE: DNA
<213> ORGANISM: Artificial Sequence
<220> FEATURE:
<223> OTHER INFORMATION: MORF1-t

<400> SEQUENCE: 50
gtcataacag aacaggta                                                   18
```

<210> SEQ ID NO 51
<211> LENGTH: 18
<212> TYPE: DNA
<213> ORGANISM: Artificial Sequence
<220> FEATURE:
<223> OTHER INFORMATION: MORF2-t

<400> SEQUENCE: 51
tacctgttct gttatgac                                                    18

<210> SEQ ID NO 52
<211> LENGTH: 15
<212> TYPE: DNA
<213> ORGANISM: Artificial Sequence
<220> FEATURE:
<223> OTHER INFORMATION: MORF1-u

<400> SEQUENCE: 52
tcaagacaga aggat                                                       15

<210> SEQ ID NO 53
<211> LENGTH: 15
<212> TYPE: DNA
<213> ORGANISM: Artificial Sequence
<220> FEATURE:
<223> OTHER INFORMATION: MORF2-u

<400> SEQUENCE: 53
atccttctgt cttga                                                       15

<210> SEQ ID NO 54
<211> LENGTH: 15
<212> TYPE: DNA
<213> ORGANISM: Artificial Sequence
<220> FEATURE:
<223> OTHER INFORMATION: MORF1-v

<400> SEQUENCE: 54
tagcaacata ggaag                                                       15

<210> SEQ ID NO 55
<211> LENGTH: 15
<212> TYPE: DNA
<213> ORGANISM: Artificial Sequence
<220> FEATURE:
<223> OTHER INFORMATION: MORF2-v

<400> SEQUENCE: 55
cttcctatgt tgcta                                                       15

<210> SEQ ID NO 56
<211> LENGTH: 12
<212> TYPE: DNA
<213> ORGANISM: Artificial Sequence
<220> FEATURE:
<223> OTHER INFORMATION: MORF1-w

<400> SEQUENCE: 56
cagagagcat at                                                          12

<210> SEQ ID NO 57
<211> LENGTH: 12
<212> TYPE: DNA
<213> ORGANISM: Artificial Sequence
<220> FEATURE:

```
<223> OTHER INFORMATION: MORF2-w

<400> SEQUENCE: 57
atatgctctc tg                                                          12

<210> SEQ ID NO 58
<211> LENGTH: 12
<212> TYPE: DNA
<213> ORGANISM: Artificial Sequence
<220> FEATURE:
<223> OTHER INFORMATION: MORF1-x

<400> SEQUENCE: 58
caagaggtac at                                                          12

<210> SEQ ID NO 59
<211> LENGTH: 12
<212> TYPE: DNA
<213> ORGANISM: Artificial Sequence
<220> FEATURE:
<223> OTHER INFORMATION: MORF2-x

<400> SEQUENCE: 59
atgtacctct tg                                                          12

<210> SEQ ID NO 60
<211> LENGTH: 10
<212> TYPE: DNA
<213> ORGANISM: Artificial Sequence
<220> FEATURE:
<223> OTHER INFORMATION: MORF1-y

<400> SEQUENCE: 60
aagaggtaca                                                             10

<210> SEQ ID NO 61
<211> LENGTH: 10
<212> TYPE: DNA
<213> ORGANISM: Artificial Sequence
<220> FEATURE:
<223> OTHER INFORMATION: MORF2-y

<400> SEQUENCE: 61
tgtacctctt                                                             10

<210> SEQ ID NO 62
<211> LENGTH: 10
<212> TYPE: DNA
<213> ORGANISM: Artificial Sequence
<220> FEATURE:
<223> OTHER INFORMATION: MORF1-z

<400> SEQUENCE: 62
aaggacagta                                                             10

<210> SEQ ID NO 63
<211> LENGTH: 10
<212> TYPE: DNA
<213> ORGANISM: Artificial Sequence
<220> FEATURE:
<223> OTHER INFORMATION: MORF2-z

<400> SEQUENCE: 63
tactgtcctt                                                             10
```

```
<210> SEQ ID NO 64
<211> LENGTH: 35
<212> TYPE: PRT
<213> ORGANISM: Artificial Sequence
<220> FEATURE:
<223> OTHER INFORMATION: Oligopeptide

<400> SEQUENCE: 64

Glu Val Ser Ala Leu Glu Lys Glu Val Ser Ala Leu Glu Lys Lys Asn
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 65
<211> LENGTH: 35
<212> TYPE: PRT
<213> ORGANISM: Artificial Sequence
<220> FEATURE:
<223> OTHER INFORMATION: Oligopeptide

<400> SEQUENCE: 65

Lys Val Ser Ala Leu Lys Glu Lys Val Ser Ala Leu Lys Glu Glu Val
1               5                   10                  15

Ser Ala Asn Lys Glu Lys Val Ser Ala Leu Lys Glu Lys Val Ser Ala
            20                  25                  30

Leu Lys Glu
        35

<210> SEQ ID NO 66
<211> LENGTH: 35
<212> TYPE: PRT
<213> ORGANISM: Artificial Sequence
<220> FEATURE:
<223> OTHER INFORMATION: Oligopeptide

<400> SEQUENCE: 66

Glu Val Ser Ala Leu Glu Lys Glu Val Ser Ala Leu Glu Lys Lys Asn
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 67
<211> LENGTH: 28
<212> TYPE: PRT
<213> ORGANISM: Artificial Sequence
<220> FEATURE:
<223> OTHER INFORMATION: Oligopeptide

<400> SEQUENCE: 67

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys
            20                  25

<210> SEQ ID NO 68
<211> LENGTH: 28
<212> TYPE: PRT
<213> ORGANISM: Artificial Sequence
<220> FEATURE:
<223> OTHER INFORMATION: Oligopeptide
```

<400> SEQUENCE: 68

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu
            20                  25

<210> SEQ ID NO 69
<211> LENGTH: 28
<212> TYPE: PRT
<213> ORGANISM: Artificial Sequence
<220> FEATURE:
<223> OTHER INFORMATION: Oligopeptide

<400> SEQUENCE: 69

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys
            20                  25

<210> SEQ ID NO 70
<211> LENGTH: 28
<212> TYPE: PRT
<213> ORGANISM: Artificial Sequence
<220> FEATURE:
<223> OTHER INFORMATION: Oligopeptide

<400> SEQUENCE: 70

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu
            20                  25

<210> SEQ ID NO 71
<211> LENGTH: 21
<212> TYPE: PRT
<213> ORGANISM: Artificial Sequence
<220> FEATURE:
<223> OTHER INFORMATION: Oligopeptide

<400> SEQUENCE: 71

Glu Val Ala Ala Leu Glu Lys Glu Val Ala Ala Leu Glu Lys Glu Val
1               5                   10                  15

Ala Ala Leu Glu Lys
            20

<210> SEQ ID NO 72
<211> LENGTH: 21
<212> TYPE: PRT
<213> ORGANISM: Artificial Sequence
<220> FEATURE:
<223> OTHER INFORMATION: Oligopeptide

<400> SEQUENCE: 72

Lys Val Ala Ala Leu Lys Glu Lys Val Ser Ala Leu Lys Glu Lys Val
1               5                   10                  15

Ser Ala Leu Lys Glu
            20

<210> SEQ ID NO 73
<211> LENGTH: 21
<212> TYPE: PRT
<213> ORGANISM: Artificial Sequence
<220> FEATURE:

<223> OTHER INFORMATION: Oligopeptide

<400> SEQUENCE: 73

Glu Val Ala Ala Leu Glu Lys Glu Val Ala Ala Leu Glu Lys Glu Val
1               5                   10                  15

Ala Ala Leu Glu Lys
            20

<210> SEQ ID NO 74
<211> LENGTH: 21
<212> TYPE: PRT
<213> ORGANISM: Artificial Sequence
<220> FEATURE:
<223> OTHER INFORMATION: Oligopeptide

<400> SEQUENCE: 74

Lys Val Ala Ala Leu Lys Glu Lys Val Ser Ala Leu Lys Glu Lys Val
1               5                   10                  15

Ser Ala Leu Lys Glu
            20

<210> SEQ ID NO 75
<211> LENGTH: 21
<212> TYPE: PRT
<213> ORGANISM: Artificial Sequence
<220> FEATURE:
<223> OTHER INFORMATION: Oligopeptide

<400> SEQUENCE: 75

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 76
<211> LENGTH: 21
<212> TYPE: PRT
<213> ORGANISM: Artificial Sequence
<220> FEATURE:
<223> OTHER INFORMATION: Oligopeptide

<400> SEQUENCE: 76

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 77
<211> LENGTH: 21
<212> TYPE: PRT
<213> ORGANISM: Artificial Sequence
<220> FEATURE:
<223> OTHER INFORMATION: Oligopeptide

<400> SEQUENCE: 77

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 78
<211> LENGTH: 21
<212> TYPE: PRT
<213> ORGANISM: Artificial Sequence

```
<220> FEATURE:
<223> OTHER INFORMATION: Oligopeptide

<400> SEQUENCE: 78

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 79
<211> LENGTH: 21
<212> TYPE: PRT
<213> ORGANISM: Artificial Sequence
<220> FEATURE:
<223> OTHER INFORMATION: Oligopeptide

<400> SEQUENCE: 79

Glu Ile Ala Ala Leu Glu Lys Glu Ile Ala Ala Leu Glu Lys Glu Ile
1               5                   10                  15

Ala Ala Leu Glu Lys
            20

<210> SEQ ID NO 80
<211> LENGTH: 21
<212> TYPE: PRT
<213> ORGANISM: Artificial Sequence
<220> FEATURE:
<223> OTHER INFORMATION: Oligopeptide

<400> SEQUENCE: 80

Lys Ile Ala Ala Leu Lys Glu Lys Ile Ser Ala Leu Lys Glu Lys Ile
1               5                   10                  15

Ser Ala Leu Lys Glu
            20

<210> SEQ ID NO 81
<211> LENGTH: 21
<212> TYPE: PRT
<213> ORGANISM: Artificial Sequence
<220> FEATURE:
<223> OTHER INFORMATION: Oligopeptide

<400> SEQUENCE: 81

Glu Ile Ala Ala Leu Glu Lys Glu Ile Ala Ala Leu Glu Lys Glu Ile
1               5                   10                  15

Ala Ala Leu Glu Lys
            20

<210> SEQ ID NO 82
<211> LENGTH: 21
<212> TYPE: PRT
<213> ORGANISM: Artificial Sequence
<220> FEATURE:
<223> OTHER INFORMATION: Oligopeptide

<400> SEQUENCE: 82

Lys Ile Ala Ala Leu Lys Glu Lys Ile Ser Ala Leu Lys Glu Lys Ile
1               5                   10                  15

Ser Ala Leu Lys Glu
            20

<210> SEQ ID NO 83
<211> LENGTH: 35
<212> TYPE: PRT
```

```
<213> ORGANISM: Artificial Sequence
<220> FEATURE:
<223> OTHER INFORMATION: Oligopeptide

<400> SEQUENCE: 83

Lys Val Ser Ala Leu Lys Glu Lys Val Ser Ala Leu Lys Glu Glu Val
1               5                   10                  15

Ser Ala Asn Lys Glu Lys Val Ser Ala Leu Lys Glu Lys Val Ser Ala
            20                  25                  30

Leu Lys Glu
        35
```

COMPOSITIONS AND METHODS FOR USING ALBUMIN-BASED NANOMEDICINES

STATEMENT REGARDING FEDERALLY SPONSORED RESEARCH OR DEVELOPMENT

This invention was made with government support under grant number GM095606 awarded by the National Institutes of Health. The government has certain rights in the invention.

BACKGROUND OF THE INVENTION

Drug free macromolecular therapeutic platforms possess great potential for treatment of several diseases and disorders. For example, the cross-linking of CD20 followed by the induction of apoptosis as described herein can be used to treat several diseases and disorders including B cell malignancies, inflammatory disorders, and autoimmune diseases with B cell involvement.

In 2015 in the United States, there were an estimated 71,850 new cases of Non-Hodgkin lymphoma (NHL) and 19,790 deaths in both males and females. Of the heterogeneous group of NHLs the majority (85-90%) derive from B lymphocytes and the remaining develop from T lymphocytes or natural killer cells. B cell lymphomas (B cell NHL) include Burkitt's, diffuse large B cell, follicular, immunoblastic large cell, precursor B-lymphoblastic, and mantle cell lymphomas. These malignancies are generally classified as either indolent or aggressive, which then dictates the type of therapy the patient may receive. The current standard of B cell NHL treatment is rituximab (the most commonly used anti-CD20 mAb) in combination with chemotherapy. However, large populations of patients exist who do not respond or develop resistance to these therapies. For example, the overall response rates for the treatment of relapsed/refractory low-grade or follicular NHL typically ranged from 40 to 50% (complete response 6, 3, 17, 3, and 14%; overall response 48, 46, 47, 39, and 43% in five different clinical trials). The non-responsiveness and/or resistance have been attributed to the inability of immune effector cells (e.g., macrophages, natural killer cells) to hypercrosslink ligated mAbs, and Fc receptor (FcR)-mediated endocytosis or "trogocytosis" of CD20 antigens. These clinical obstacles create the need for new, improved therapeutic strategies.

CD20 is a 35-37 kDa integral membrane protein highly expressed on more than 95% of B-cell lymphomas. Free CD20 antigen is not present in serum, and there is no known natural ligand of CD20. When bound by antibodies, CD20 has a very low intracellular internalization rate; it is often considered a non-internalizing receptor. Studies suggest that CD20 functions as a store-operated calcium channel and a cell cycle regulator. It is one of the most reliable biomarkers of B-lymphocytes, thus providing an ideal target for treatment of B cell NHL. CD20 is also expressed on normal B cells; however, it is not expressed on stem cells or progenitor cells and mature or activated plasma cells. Therefore, the "B-cell depletion" therapeutic approach is considered safe; normal numbers of B cells can be restored after treatment. The therapeutic efficacy of anti-CD20 mAbs is ascribed to three cellular events: antibody-dependent cellular cytotoxicity (ADCC), complement-dependent cytotoxicity (CDC), and CD20-mediated apoptosis. All of these mechanisms require immune effector cells to function. In contrast, drug-free macromolecular therapeutics trigger direct and specific apoptosis of B-cell lymphomas without the help of effector cells. This is achieved by the design of synthetic effectors that reproduce the function of immune effector cells.

There is still a scarcity of compositions and methods that are effective in inducing apoptosis and for the treatment of B cell malignancies, inflammatory disorders, and autoimmune diseases with B cell involvement. These needs and other needs are satisfied by the present invention.

BRIEF SUMMARY OF THE INVENTION

Disclosed are methods of inducing apoptosis, the method comprising contacting a population of cells with a first conjugate comprising a targeting moiety and a first oligomerization moiety, and contacting a population of cells with a second conjugate comprising albumin and one or more second oligomerization moieties, wherein the contacting of the cells with the first conjugate and the second conjugate induces apoptosis of the cells. In some aspects, oligomerization moieties can be oligonucleotides or oligopeptides.

Also disclosed are methods of inducing apoptosis, the method comprising contacting a population of cells with a first conjugate comprising a targeting moiety and a morpholino oligonucleotide (morpholino; MORF), and contacting a population of cells with a second conjugate comprising albumin and one or more morpholinos, wherein the contacting of the cells with the first conjugate and the second conjugate induces apoptosis of the cells.

Also disclosed are methods of inducing apoptosis, the method comprising contacting a population of cells with a first conjugate comprising a targeting moiety and a oligopeptide, and contacting a population of cells with a second conjugate comprising albumin and one or more oligopeptides, wherein the contacting of the cells with the first conjugate and the second conjugate induces apoptosis of the cells.

Disclosed are methods of inducing apoptosis, the method comprising contacting a population of cells with a composition comprising a first conjugate comprising a targeting moiety and a first oligomerization moiety and a second conjugate comprising albumin and one or more second oligomerization moieties, wherein the contacting of the cells with the composition induces apoptosis of the cells. In some aspects, oligomerization moieties can be oligonucleotides or oligopeptides.

Also disclosed are methods of inducing apoptosis, the method comprising contacting a population of cells with a composition comprising a first conjugate comprising a targeting moiety and a morpholino and a second conjugate comprising a conjugate comprising albumin and one or more morpholinos, wherein the contacting of the cells with the composition induces apoptosis of the cells.

Also disclosed are methods of inducing apoptosis, the method comprising contacting a population of cells with a composition comprising a first conjugate comprising a targeting moiety and a oligopeptide and a second conjugate comprising a conjugate comprising albumin and one or more oligopeptides, wherein the contacting of the cells with the composition induces apoptosis of the cells.

Disclosed are kits comprising a first conjugate comprising a targeting moiety and a oligomerization moiety, and a second conjugate comprising albumin and one or more oligomerization moieties.

Disclosed are kits comprising a first conjugate comprising a targeting moiety and an oligonucleotide, and a second conjugate comprising albumin and one or more oligonucleotides. Oligonucleotides can be morpholinos. Thus, disclosed are kits comprising a first conjugate comprising a targeting moiety and a morpholino, and a second conjugate comprising albumin and one or more morpholinos.

Disclosed are kits comprising a first conjugate comprising a targeting moiety and an oligopeptide, and a second conjugate comprising albumin and one or more oligopeptides.

BRIEF DESCRIPTION OF THE SEVERAL VIEWS OF THE DRAWINGS

The accompanying Figures, which are incorporated in and constitute a part of this specification, illustrate several aspects of the invention and together with the description serve to explain the principles of the invention.

Figure 1:
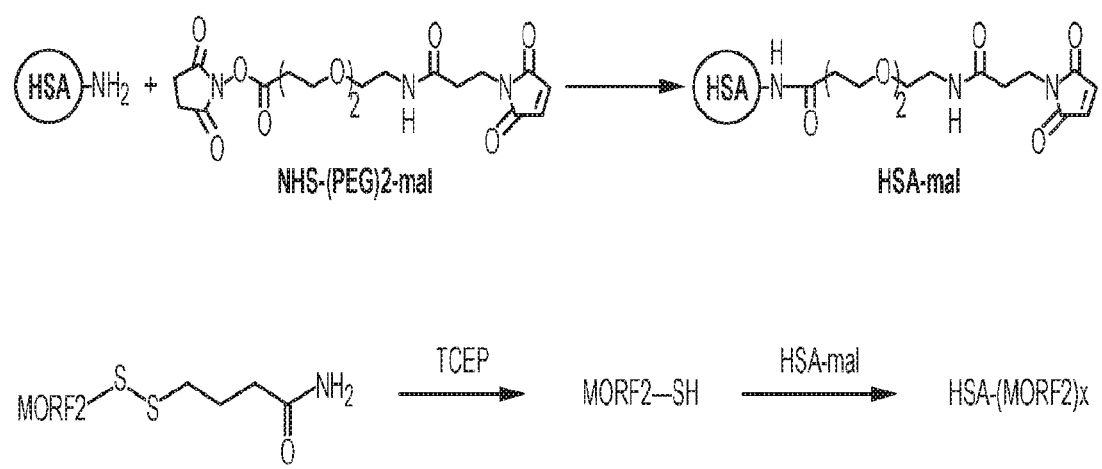
FIG. 1 shows a schematic of the synthesis of nanoconjugate HSA-(MORF2)$_x$.

Additional advantages of the invention are set forth in part in the description that follows, and in part will be obvious from the description, or can be learned by practice of the invention. It is to be understood that both the foregoing general description and the following detailed description are exemplary and are not restrictive of the invention as claimed.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. For example, in an aspect, a conjugate comprising a targeting moiety and an oligonucleotide can optionally comprise a detectable label. In an aspect, a disclosed method can optionally comprise repeating the administration of a disclosed composition and/or conjugate.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, "homolog" or "homologue" refers to a polypeptide or nucleic acid with homology to a specific known sequence. Specifically disclosed are variants of the nucleic acids and polypeptides herein disclosed which have at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more percent homology to the stated or known sequence. Those of skill in the art readily understand how to determine the homology of two or more proteins or two or more nucleic acids. For example, the homology can be calculated after aligning the two or more sequences so that the homology is at its highest level. It is understood that one way to define any variants, modifications, or derivatives of the disclosed genes and proteins herein is through defining the variants, modification, and derivatives in terms of homology to specific known sequences.

As used herein, "aptamers" refer to molecules that interact with a target molecule, preferably in a specific way. Typically, aptamers are small nucleic acids ranging from 15-50 bases in length that fold into defined secondary and tertiary structures, such as stem-loops or G-quartets. Aptamers can bind small molecules and large molecules. Aptamers can bind very tightly with Kd's from the target molecule of less than $10^{-12}$ M. Aptamers can bind the target molecule with a very high degree of specificity. Aptamers are known to the art and representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

As used herein, a "targeting moiety" can be specific to a recognition molecule on the surface of a cell or a population of cells, such as, for example B cells. In an aspect of the disclosed compositions and methods, a targeting moiety can include, but is not limited to: a monoclonal antibody, a polyclonal antibody, full-length antibody, a chimeric antibody, Fab', Fab, F(ab)$_2$, F(ab')$_2$, a single domain antibody (DAB), Fv, a single chain Fv (scFv), a minibody, a diabody, a triabody, hybrid fragments, a phage display antibody, a ribosome display antibody, an oligonucleotide, a modified oligonucleotide, a peptide, a peptide ligand, a hormone, a growth factor, a cytokine, a saccharide or polysaccharide, and an aptamer.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient.

A patient refers to a subject afflicted with one or more diseases or disorders, such as, for example, a B cell malignancy, an inflammatory disorder, and an autoimmune disease with B cell involvement. In an aspect, diseases and disorders include, but are not limited to: non-Hodgkin's lymphoma, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a patient has JC virus. In an aspect, a patient has received an organ transplant. In an aspect of a disclosed method, a patient has been diagnosed with a need for treatment of one or more of the aforementioned diseases or disorders prior to the administering step. In an aspect of a disclosed method, a patient has been diagnosed with a need for inducing apoptosis of malignant cells, such as, for example, malignant B cells.

As used herein, "non-Hodgkin's lymphoma" or "NHL" refers to a cancer of the lympathic tissue. As a heterogenous condition, NHL can cause enlargement of lymph nodes and generalized systems.

As used herein, the term "treatment" refers to the medical management of a patient with the intent to cure, ameliorate, stabilize, or prevent a disease, pathological condition, or disorder (such as, for example, B-cell malignancies, inflammatory disorders, and autoimmune diseases with B cell involvement). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In an aspect, preventing malignant cell growth is intended.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with NHL" means having been subjected to a physical examination by a person of skill, for example, a physician, and found to have a condition that can be diagnosed or can be treated by a compound or composition that can prevent or inhibit malignant cell growth and/or induce apoptosis in a population of cells, such as B cells. As a further example, "diagnosed with a need for inducing apoptosis" refers to having been subjected to a physical examination by a person of skill, for example, a physician, and found to have a condition characterized by malignant cell growth or other disease wherein inducing apoptosis of a population of cells would be beneficial to the subject. Such a diagnosis can be in reference to a disorder, such as NHL, and the like, as discussed herein.

As used herein, "one or more oligonucleotides" can refer to "one or more morpholinos". For example, in an aspect a disclosed conjugate comprising albumin can comprise one or more grafted oligonucleotides or can comprise one or more grafted morpholinos. In an aspect, "one or more oligonucleotides" or "one or more morpholinos" can comprise 1 morpholino, or 2 morpholinos, or 3 morpholinos, or 4 morpholinos, or 5 morpholinos, or 6 morpholinos, or 7 morpholinos, or 8 morpholinos, or 9 morpholinos, or 10 morpholinos. For example, in an aspect, a disclosed conjugate comprising albumin can comprise 1 morpholino. In an aspect, a disclosed conjugate comprising albumin can comprise 3 morpholinos. In an aspect, a disclosed conjugate comprising albumin can comprise 10 morpholinos. In an aspect, a disclosed conjugate comprising albumin can comprise more than 10 grafted morpholinos. In an aspect, the one or more morpholinos can comprise one or more grafted MORF2 morpholinos. For example, a disclosed albumin-MORF2 conjugate can comprise 1 grafted morpholino, or 3 grafted morpholinos, or 10 grafted morpholinos, or 10 grafted morpholinos, or more than 10 grafted morpholinos. For example, a disclosed albumin-MORF2 conjugate can comprise 1 grafted MORF2, or 3 grafted MORF2, or 10 grafted MORF2, or 15 grafted MORF2, or more than 15 grafted MORF2.

As used herein, the phrase "identified to be in need of treatment for a disorder," or the like, refers to selection of a subject based upon need for treatment of the disorder. For example, a subject can be identified as having a need for treatment of a disorder (e.g., NHL or some other disorder related to malignant cell growth or a disorder requiring apoptosis of a population of cells) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who performed the diagnosis.

As used herein, the terms "administering" and "administration" refer to any method of providing a disclosed composition, conjugate, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration for a disclosed composition or a disclosed conjugate so as to treat a subject or induce apoptosis. In an aspect, the skilled person can also alter or modify an aspect of an administering step so as to improve efficacy of a disclosed conjugate or disclosed composition.

As used herein, "altering one or more administering steps" can comprise changing or modifying the administration of one or more disclosed compositions or disclosed conjugatees. In an aspect, administering the conjugate comprising a targeting moiety and an oligonucleotide can be altered, for example, by changing the route of administration, or changing the dose of the composition, or changing the timing of administration, or changing the frequency of the administration, or a combination thereof. In an aspect, administering the conjugate comprising a copolymer carrier and one or more oligonucleotides can be altered, for example, by changing the route of administration, or changing the dose of the composition, or changing the timing of administration, or changing the frequency of the administration, or a combination thereof. In an aspect, altering one or more administering steps can comprise altering the administering of the conjugate comprising a targeting moiety and an oligonucleotide and altering the administering of a conjugate comprising albumin and one or more oligonucleotides.

The term "contacting" as used herein refers to bringing a disclosed composition, compound, or conjugate together with an intended target (such as, e.g., a cell or population of cells, a receptor, an antigen, or other biological entity) in such a manner that the disclosed composition, compound, or conjugate can affect the activity of the intended target (e.g., receptor, transcription factor, cell, population of cells, etc.), either directly (i.e., by interacting with the target itself), or indirectly (i.e., by interacting with another molecule, co-factor, factor, or protein on which the activity of the target is dependent). In an aspect, a disclosed composition or conjugate can be contacted with a cell or population of cells, such as, for example, B cells.

As used herein, the term "determining" can refer to measuring or ascertaining an activity or an event or a quantity or an amount or a change in expression and/or in activity level or in prevalence and/or incidence. For example, determining can refer to measuring or ascertaining the quantity or amount of apoptotic induction. Determining can also refer to measuring or ascertaining the quantity or amount of caspase activity or expression. Methods and techniques used to determining an activity or an event or a quantity or an amount or a change in expression and/or in activity level or in prevalence and/or incidence as used herein can refer to the steps that the skilled person would take to measure or ascertain some quantifiable value. The art is familiar with the ways to measure an activity or an event or a quantity or an amount or a change in expression and/or in activity level or in prevalence and/or incidence As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. For example, in an aspect, an effective amount of a disclosed composition or conjugate is the amount effective to induce apoptosis in a desired cell or population of cells. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a disclosed composition or conjugate at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. In an aspect, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

The term "oligomerization moiety" refers to a moiety that promotes or allows the oligomerization of a first oligomerization moiety to one or more second oligomerization moieties. For example, an "oligomerization moiety" can be an oligonucleotide, oligopeptide or an oligosaccharide.

B. Compositions

The disclosed conjugates can be used in the disclosed methods of inducing apoptosis and methods of treatment disclosed herein.

i) Conjugate Comprising Targeting Moiety and Oligomerization Moiety

Disclosed herein are conjugates comprising a targeting moiety and an oligomerization moiety. For example, the oligomerization moiety can be an oligonucleotide or an oligopeptide.

In an aspect, a disclosed conjugates can further comprises a detectable label. Detectable labels are known to one of skill in the art and include, but are not limited to: rhodamine, FITC, Cy3, Cy3.5, Cy5, Texas Red, Alexa Fluor 488, Alexa Fluor 610, Alexa Fluor 647, and Alexa Fluor 750.

(a) Targeting Moiety

Disclosed are targeting moieties that can be bound, linked, or attached to an oligomerization moiety such as, but not limited to, an oligonucleotide or an oligopeptide.

In an aspect of a disclosed conjugate, a targeting moiety can be specific for a non-internalizing cell surface molecule or slowly internalizing cell surface molecule. Examples of a non-internalizing cell surface molecule or a slowly internalizing cell surface molecule are known to one of skill in the art. In an aspect, a non-internalizing cell surface molecule or slowly internalizing cell surface molecule can be on a cell or a population of cells. In an aspect, a cell or a population of cells can be B cells. In an aspect, the B cells can be normal B cells. In an aspect, the B cells can be malignant B cells.

In an aspect of a disclosed conjugate, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18 (TNFRSF18). In an aspect, a receptor can be a TNF-like weak inducer of apoptosis receptor (TWEAK or TNFSF12).

In an aspect of a disclosed conjugate, a targeting moiety can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamer. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PRO131921, BCD-020, IBI-301, ublituximab, and BLX-301. In an aspect, the anti-CD20 receptor antibody can be 1F5.

(b) Oligomerization Moiety

An oligomerization moiety can be any compound (e.g. oligopeptides, oligonucleotides, or oligosaccharides) that can bind to or interact with at least one other oligerization moiety to form a complex.

Disclosed are oligomerization moieties that can be bound, linked, or attached to a targeting moiety or albumin.

(i) Oligonucleotides

Oligonucleotides are well known to the art. In an aspect of a disclosed conjugate, an oligonucleotide can be biocompatible. In an aspect, an oligonucleotide can be non-degradable. In an aspect, an oligonucleotide can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed conjugate, an oligonucleotide can be a peptide nucleic acid. In an aspect, an oligonucleotide can be a phosphodiester. In an aspect, an oligonucleotide can be a phosphorothioate. In an aspect, an oligonucleotide can be a peptide nucleic acid. In an aspect, an oligonucleotide can be a 2'-O-methyl phosphodiester. In an aspect, an oligonucleotide can be a locked oligonucleotide. In an aspect, an oligonucleotide can be a morpholino.

(a) Morpholinos

The compositions and methods disclosed herein can utilize a biocompatible, synthetic oligonucleotide analogue with a chemically modified backbone. The schematic shown below lists several analogues and compares the properties of these analogues with natural DNA.

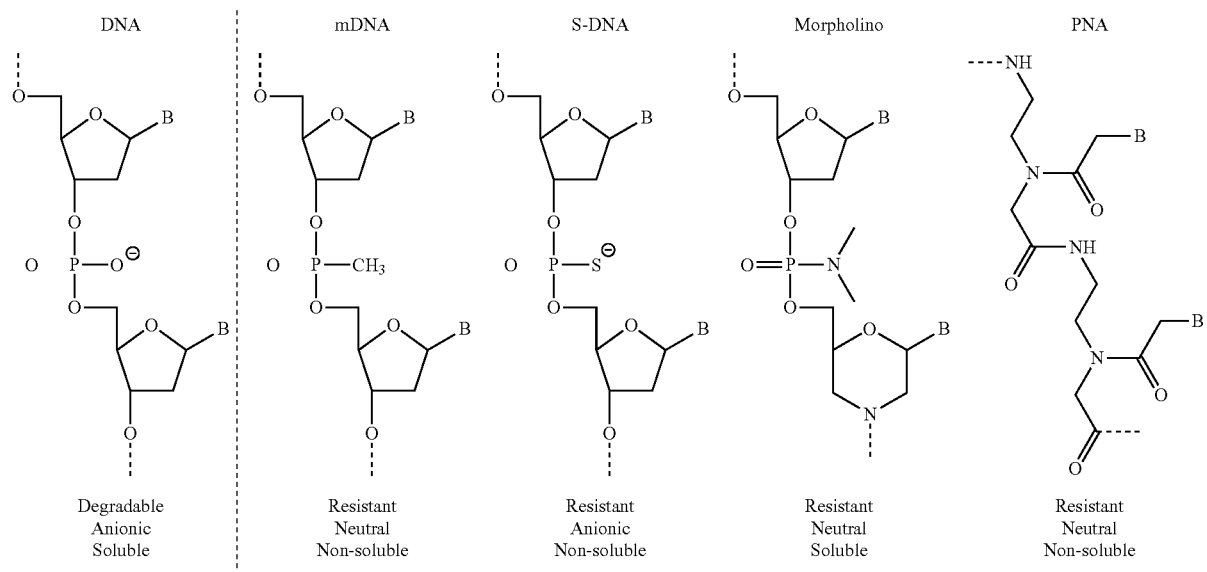

Preferably, the analogue can be biocompatible and non-degradable, the disclosed compositions and methods can utilize phophorodiamidate morpholino oligonucleotides (also known as morpholinos or MORFs). As used herein, the term "MORF" refers to a morpholino. For example, "MORF1" can refer to a first morpholino and "MORF2" can refer to a second morpholino. In some aspects MORF1 and MORF2 are capable of oligomerizing. Morpholinos have a chemically-modified, non-charged backbone and are assembled from four different subunits, each of which contains one of the four nucleobases (A, T, G, and C) linked to a 6-membered morpholine ring. The subunits are joined by non-ionic phosphordiamidate linkages to generate a morpholino oligonucleotide. Morpholinos also possess strong binding affinity (i.e., Kd from the low nM to pM levels), high sequence specificity, and well-demonstrated safety profiles. Furthermore, the immunogenicity of morpholinos is highly sequence dependent, and therefore, can be addressed. The synthesis, structures, and binding characteristics of morpholinos are detailed in U.S. Pat. Nos. 5,698,685, 5,217,866, 5,142,047, 5,034,506, 5,166,315, 5,521,063, and 5,506,337, each of which are incorporated herein by reference in its entirety.

A disclosed morpholino having a longer length provides a higher specificity and a stronger binding affinity; however, such morpholinos also have poorer water-solubility. In the art, a 14 bp-15 bp morpholino is considered the minimal length necessary to maintain ideal targeting effects. A 25 bp morpholino can ensure strong binding affinity and good water-solubility (about 5-30 mM). For example, using 25 bp morpholinos in the disclosed compositions and methods can avoid the impact of steric hindrance on the hybridization of a first and second morpholino (e.g. MORF1 and MORF2). A longer sequence can provide better "steric flexibility" for hybridization. Accordingly, in the compositions and methods disclosed herein, morpholinos can comprise 10 bp-40 bp. In an aspect, for example, a morpholino can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length.

The A/T/C/G content of a disclosed morpholino can be determined based on three factors: (1) G+C content (# or % of G's and C's), (2) G content (# or % of G's), and (3) C content (# or % of C's).

Regarding G+C content, a disclosed morpholino can comprise a G+C content of about 35% to about 65%. This range can provide optimal binding efficacy and specificity. Regarding G content, a disclosed morpholino can comprise a G content of less than about 36%. This level of G content can provide good aqueous solubility; however, repeats of 4 or more G's should be avoided. Regarding C content, a disclosed morpholino can comprise a C content of less than 7. This level of C content can ensure that the unfavorable effect of enhancing kidney accumulation of a morpholino can be avoided. Furthermore, conjugation of one or more morpholinos with albumin can favorably alter the pharmacokinetic profiles of the morpholinos and can reduce kidney accumulation (as compared to conjugation of morpholinos and Fab' fragment). Table 1 shows the kidney accumulation of morpholinos comprising varying levels of C content. The morpholino having 25 C's had the highest percent accumulation in the kidneys of normal mice just 3 hours post-injection. (Liu et al., 2004).

TABLE 1

| Sequences of $^{99m}$Tc-labeled MORFs | SEQ ID NO. | # of C's | % ID/ Kidneys |
|---|---|---|---|
| 5' AAAAAAAAAAAAAAAAAAAAAAAAA 3' | SEQ ID NO. 53 | 0 | 0.9 |
| 5' TTTTTTTTTTTTTTTTTTTTTTTTT 3' | SEQ ID NO. 54 | 0 | 3.1 |
| 5' AAGAAGAAGAAGAAGAAGAAGA 3' | SEQ ID NO. 55 | 0 | 2.8 |
| 5' TAGTTGTGACGTACA 3' | SEQ ID NO. 56 | 2 | 1.7 |
| 5' ATCAACACTGCTTGT 3' | SEQ ID NO. 57 | 4 | 4.5 |
| 5' ATCAACACTGCTTGTGGG 3' | SEQ ID NO. 58 | 4 | 4.7 |
| 5' ATCAACACTGCTTGTGGGTGGTGGT 3' | SEQ ID NO. 59 | 4 | 5.6 |

TABLE 1-continued

| Sequences of $^{99m}$Tc-labeled MORFs | SEQ ID NO. | # of C's | % ID/ Kidneys |
|---|---|---|---|
| 5' TAGTTGTGACGTACACCC 3' | SEQ ID NO. 60 | 5 | 4.9 |
| 5' TAGTTGTGACGTACACCCACCACCA 3' | SEQ ID NO. 61 | 9 | 13.5 |
| 5' CACCACCCCCTCGCTGGTC 3' | SEQ ID NO. 62 | 11 | 20.9 |
| 5' CCCCCCCCCCCCCCCCCCCCCCCCC 3' | SEQ ID NO. 63 | 25 | 80.8 |

In the disclosed compositions and methods, a morpholino conjugated to the Fab' fragment can comprise more A's and less C's whereas the one or more morpholinos conjugated to the albumin carrier can comprise more C's and less A's. Accordingly, in an aspect, a 25 bp morpholino can comprise 3 C's, 6 G's, 12 A's, 4 T's (G+C=36%, G=24%). A complementary 25 bp morpholino can comprise 6 C's, 3 G's, 4 A's, 12 T's (G+C=36%, G=12%).

After the nucleobase composition of each morpholino is determined, a publically accessible, online sequence "scrambler" can be used to ensure minimal off-target binding with human mRNA. Furthermore, publically accessible, online sequence analysis software can be used to ensure minimal self-complementarity. In the experiments disclosed herein, when performing sequence analysis to avoid self-complementarity, the "Minimum base pairs required for self-dimerization" and "Minimum base pairs required for a hairpin" were set to "2" and "2" (for 10 bp and 12 bp); "3" and "3" (for 15 bp, 18 bp, 20 bp, 23 bp, and 25 bp); "4" and "4" (for 28 bp, 30 bp, 32 bp, and 35 bp); and "5" and "4" (for 38 bp and 40 bp). Table 2 provides a listing of exemplary morpholinos for use in the disclosed compositions and methods.

TABLE 2

Listing of Exemplary Morpholinos

| MORF # (SEQ ID NO:) | MORF Sequences | Length (bp) | Content G + C | G |
|---|---|---|---|---|
| MORF1-a (SEQ ID NO: 1) | 5' GAA CTA ATG CAA TAA CTA TCA CGA ATG CGG GTA ACT TAA T 3' | 40 | 35% | 17.5% |
| MORF2-a (SEQ ID NO: 2) | 5' ATT AAG TTA CCC GCA TTC GTG ATA GTT ATT GCA TTA GTT C 3' | 40 | 35% | 17.5% |
| MORF1-b (SEQ ID NO: 3) | 5' GAA ACC GCT ATT TAT TGG CTA AGA ACA GAT ACG AAT CAT A 3' | 40 | 35% | 17.5% |
| MORF2-b (SEQ ID NO: 4) | 5'-TAT GAT TCG TAT CTG TTC TTA GCC AAT AAA TAG CGG TTT C 3' | 40 | 35% | 17.5% |
| MORF1-c (SEQ ID NO: 5) | 5' GTA AAC GCG ACA AAT GCC GAT AAT GCT TCG ATA ATA AT 3' | 38 | 37% | 18.5% |
| MORF2-c (SEQ ID NO: 6) | 5' ATT ATT ATC GAA GCA TTA TCG GCA TTT GTC GCG TTT AC 3' | 38 | 37% | 18.5% |
| MORF1-d (SEQ ID NO: 7) | 5' GAC AGA GTT CAC TAT GAC AAA CGA TTT CAC GAG TAA TA 3' | 38 | 37% | 18.5% |
| MORF2-d (SEQ ID NO: 8) | 5' TAT TAC TCG TGA AAT CGT TTG TCA TAG TGA ACT CTG TC 3' | 38 | 37% | 18.5% |
| MORF1-e (SEQ ID NO: 9) | 5' CCT GAT ACA GAA GTA GAA AGC AGT CAC GCA ATA TA 3' | 35 | 40% | 20% |
| MORF2-e (SEQ ID NO: 10) | 5' TAT ATT GCG TGA CTG CTT TCT ACT TCT GTA TCA GG 3' | 35 | 40% | 20% |
| MORF1-f (SEQ ID NO: 11) | 5' GAA CAA CGA GAG GTG CTC AAT ACA GAT ATC AAT CA 3' | 35 | 40% | 20% |
| MORF2-f (SEQ ID NO: 12) | 5' TGA TTG ATA TCT GTA TTG AGC ACC TCT CGT TGT TC 3' | 35 | 40% | 20% |
| MORF1-g (SEQ ID NO: 13) | 5' AGT CAT AGA TAG ACA GAA TAG CCG GAT AAA CT 3' | 32 | 38% | 22% |
| MORF2-g (SEQ ID NO: 14) | 5' AGT TTA TCC GGC GTC TAT TCT TAT CTA TGA CT 3' | 32 | 38% | 16% |
| MORF1-h (SEQ ID NO: 15) | 5' GAT ACA GAA GTA GAA AGC AGT CAC GCA ATA TA 3' | 32 | 38% | 22% |
| MORF2-h (SEQ ID NO: 16) | 5' TAT ATT GCG TGA CTG CTT TCT ACT TCT GTA TC 3' | 32 | 38% | 16% |
| MORF1-i (SEQ ID NO: 17) | 5' GGC ATA GAT AAC AGA ATA GCC GGA TAA ACT 3' | 30 | 40% | 23% |
| MORF2-i (SEQ ID NO: 18) | 5' AGT TTA TCC GGC TAT TCT GTT ATC TAT GCC 3' | 30 | 40% | 17% |
| MORF1-j (SEQ ID NO: 19) | 5' GAC CAG TAG ATA AGT GAA CCA GAT TGA ACA 3' | 30 | 40% | 23% |
| MORF2-j (SEQ ID NO: 20) | 5' TGT TCA ATC TGG TTC ACT TAT CTA CTG GTC 3' | 30 | 40% | 17% |
| MORF1-k (SEQ ID NO: 21) | 5' GAG TAC AGC CAG AGA GAA TCA ATA T A 3' | 28 | 39% | 25% |
| MORF2-k (SEQ ID NO: 22) | 5' TAT ATT GAT TCT CTC TGG CTG TAC T C 3' | 28 | 39% | 14% |
| MORF1-l (SEQ ID NO: 23) | 5' GTG AAC ACG AAA GAG TGA CGC AAT AAA T 3' | 28 | 39% | 25% |
| MORF2-l (SEQ ID NO: 24) | 5' ATT TAT TGC GTC ACT CTT TCG TGT TCA C 3' | 28 | 39% | 14% |

TABLE 2-continued

Listing of Exemplary Morpholinos

| MORF # (SEQ ID NO:) | MORF Sequences | Length (bp) | Content G + C | G |
|---|---|---|---|---|
| MORF1-m (SEQ ID NO: 25) | 5' GAG TAA GCC AAG GAG AAT CAA TAT A 3' | 25 | 36% | 24% |
| MORF2-m (SEQ ID NO: 26) | 5' TAT ATT GAT TCT CCT TGG CTT ACT C 3' | 25 | 36% | 12% |
| MORF1-n (SEQ ID NO: 27) | 5' AGA TGA CGA TAA AGA CGC AAA GAT T 3' | 25 | 36% | 24% |
| MORF2-n (SEQ ID NO: 28) | 5' AAT CTT TGC GTC TTT ATC GTC ATC T 3' | 25 | 36% | 12% |
| MORF1-o (SEQ ID NO: 29) | 5' GGA CCA AGT AAA CAG GGA TAT AT 3' | 23 | 39% | 26% |
| MORF2-o (SEQ ID NO: 30) | 5' ATA TAT CCC TGT TTA CTT GGT CC 3' | 23 | 39% | 13% |
| MORF1-p (SEQ ID NO: 31) | 5' GCT GAA AAC CAA TAT GAG AGT GA 3' | 23 | 39% | 26% |
| MORF2-p (SEQ ID NO: 32) | 5' TCA CTC TCA TAT TGG TTT TCA GC 3' | 23 | 39% | 13% |
| MORF1-q (SEQ ID NO: 33) | 5' GAT GAA GTA CCG ACA AGA TA 3' | 20 | 40% | 25% |
| MORF2-q (SEQ ID NO: 34) | 5' TAT CTT GTC GGT ACT TCA TC 3' | 20 | 40% | 15% |
| MORF1-r (SEQ ID NO: 35) | 5' GAC AGG ATG AAT AAC ACA GT 3' | 20 | 40% | 25% |
| MORF2-r (SEQ ID NO: 36) | 5' ACT GTG TTA TTC ATC CTG TC 3' | 20 | 40% | 15% |
| MORF1-s (SEQ ID NO: 37) | 5' GCA GCA AAC GAA GTA TAT 3' | 18 | 39% | 22% |
| MORF2-s (SEQ ID NO: 38) | 5' ATA TAC TTC GTT TGC TGC 3' | 18 | 39% | 17% |
| MORF1-t (SEQ ID NO: 39) | 5' GTC ATA ACA GAA CAG GTA 3' | 18 | 39% | 22% |
| MORF2-t (SEQ ID NO: 40) | 5' TAC CTG TTC TGT TAT GAC 3' | 18 | 39% | 17% |
| MORF1-u (SEQ ID NO: 41) | 5' TCA AGA CAG AAG GAT 3' | 15 | 40% | 27% |
| MORF2-u (SEQ ID NO: 42) | 5' ATC CTT CTG TCT TGA 3' | 15 | 40% | 13% |
| MORF1-v (SEQ ID NO: 43) | 5' TAG CAA CAT AGG AAG 3' | 15 | 40% | 27% |
| MORF2-v (SEQ ID NO: 44) | 5' CTT CCT ATG TTG CTA 3' | 15 | 40% | 13% |
| MORF1-w (SEQ ID NO: 45) | 5' CAG AGA GCA TAT 3' | 12 | 42% | 25% |
| MORF2-w (SEQ ID NO: 46) | 5' ATA TGC TCT CTG 3' | 12 | 42% | 17% |
| MORF1-x (SEQ ID NO: 47) | 5' CAA GAG GTA CAT 3' | 12 | 42% | 25% |
| MORF2-x (SEQ ID NO: 48) | 5' ATG TAC CTC TTG 3' | 12 | 42% | 17% |
| MORF1-y (SEQ ID NO: 49) | 5' AAG AGG TAC A 3' | 10 | 40% | 30% |
| MORF2-y (SEQ ID NO: 50) | 5' TGT ACC TCT T 3' | 10 | 40% | 10% |
| MORF1-z (SEQ ID NO: 51) | 5' AAG GAC AGT A 3' | 10 | 40% | 30% |
| MORF2-z (SEQ ID NO: 52) | 5' TAC TGT CCT T 3' | 10 | 40% | 10% |

In an aspect, hybridization between a pair of disclosed morpholinos can be achieved by base-pairing (i.e., specific hydrogen bonding patterns). The hybridization can be maintained by base-stacking (i.e., pi interactions).

In an aspect, the morpholinos utilized in the disclosed compositions and methods can be completely complementary (100%) or can be less than completely complementary. Therefore, in an aspect, the percent complementarity of the morpholino of the Fab'-MORF1 conjugate and the one or more morpholinos of the albumin-MORF2 conjugate can be 80-85%, 85-90%, 90-95%, or 95-100% complementary. In an aspect, the morpholino of the Fab'-MORF1 conjugate and the one or more morpholinos of the albumin-MORF2 conjugate can be 93%, 94%, 95%, 96%, 97%, 98%, 99%, or 100% complementary. In an aspect, the morpholino of the Fab'-MORF1 conjugate and the one or more morpholinos of the albumin-MORF2 conjugate can be at least 93% complementary.

In an aspect, the morpholino of the Fab'-MORF1 conjugate and the one or more morpholinos of the albumin-MORF2 conjugate can have an equilibrium dissociation constant Kd≤15 nM. In an aspect, the morpholino of the Fab'-MORF1 conjugate and the one or more morpholinos of the albumin-MORF2 conjugate can have a binding constant (Kd) smaller than $10^{-7}$ M. In an aspect, the morpholino of the Fab'-MORF1 conjugate and the one or more morpholinos of the albumin-MORF2 conjugate can have a binding constant (Kd) smaller than $10^{-9}$ M.

In an aspect, a disclosed morpholino does not bind to any mRNA target of a genome, such as, for example, the human genome. In an aspect, a disclosed morpholino is not self-complementary. In an aspect, a morpholino can be succinimidyl-4-(N-maleimidomethyl)cyclohexane-1-carboxylate (SMCC) modified.

In an aspect of a disclosed conjugate, a morpholino can be 25 bp in length and can comprise 3 cytidines, 6 guanosines, 12 adenosines, and 4 thymidines. For example, in an aspect, a morpholino comprising 3 cytidines, 6 guanosines, 12 adenosines, and 4 thymidines can be 5' GAGTAAGC-CAAGGAGAATCAATATA 3' (SEQ ID NO:25). In an aspect, a morpholino of a disclosed conjugate can comprise about 35% to about 65% GC content. In an aspect, a morpholino can comprise a G content less than 36%. In an aspect, a morpholino can comprise no more than 7 C's.

In an aspect of a disclosed conjugate, a targeting moiety can be conjugated to an oligonucleotide. Types of conjugation and methods for conjugating are known to the art. In an aspect, a targeting moiety of a disclosed conjugate can be conjugated to an oligonucleotide via, for example, a covalent bond. In an aspect, a targeting moiety can be conjugated to an oligonucleotide via a thiol group. Thiol groups are known to the art. In an aspect of a disclosed conjugate, a targeting moiety can be conjugated to an oligonucleotide via a thioether bond, a thiol-maleimide bond, a thiol-vinylsulfone bond, a thiol-halogeno bond, a thiol-pentafluorophenyl ester bond, a thiol-ene bond, or a thiol-yne bond.

Disclosed herein are conjugatees comprising a targeting moiety and an oligonucleotide, wherein the targeting moiety is a Fab' fragment, wherein the Fab' fragment is specific for a CD20 receptor, wherein the oligonucleotide is a morpholino, and wherein the Fab' fragment is conjugated to the morpholino via a thioether bond.

(ii) Oligopeptides

Oligopeptides are well known to the art. In an aspect of a disclosed conjugate, an oligopeptide can be biocompatible. In an aspect, an oligopeptide can be non-degradable. In an aspect, an oligopeptide can be water-soluble.

(a) Coiled Coil Forming Peptides

In an aspect of a disclosed conjugate, one or more coiled coil forming peptides can be bound to a targeting moiety or albumin (e.g. in a first or second conjugate, respectively).

A coiled-coil is one of the basic folding patterns of native proteins. It consists of two or more right-handed α-helices winding together to form a slightly left-handed super-helix. The primary structure of the coiled-coil motif is characterized by a sequence of repeating heptads designated as [a, b, c, d, e, f, g]$_x$, in which a and d are usually hydrophobic amino acid residues, while the others are polar. Two helices associate through a hydrophobic interface between a and d, making b, c, and f face outward. Interhelical electrostatic interactions between residues e and g contribute to the stability of the coiled-coil. Depending on their detailed structure, α-helices may associate as homodimers, heterodimers in parallel or antiparallel alignments, or form higher order (e.g., tetramer) aggregates. Examples of hydrophobic amino acids are Val, Ile, Leu, Met, Tyr, Phe and Trp.

Two or more coiled coil forming peptides can interact by forming helices with each other. The coiled coil forming peptides can be any amino acid sequence that forms a coiled coil structure. While the exemplified coiled coil domains herein are those cloned from a variety of proteins, it is understood that various mutations and derivatization are encompassed by the invention, so long as the resultant coiled coil domain is recognized by a person of skill in the art as a coiled coil structure and the coiled coil domain containing chimera is capable of forming a multimer, is easily soluble, and is able to provide similar or greater potency with respect to the native ligand or receptor.

The coiled coil forming peptides can be those naturally occurring peptides or chimeric coiled coil forming peptides. Chimeric coiled coil forming peptides can be a combination of naturally occurring coiled coil forming peptide fragments.

Examples of peptides for use in the methods and compositions disclosed herein are shown in Table 3.

TABLE 3

Oligopeptides (*The peptide is composed of D-amino acid residues)

| SEQ ID NO: | Name | Sequences |
|---|---|---|
| SEQ ID NO: 64 | CCE | E VSALEKE VSALEKK NSALEKE VSALEKE VSALEK |
| SEQ ID NO: 65 | CCK | K VSALKEK VSALKEE VSANKEK VSALKEK VSALKE |
| SEQ ID NO: 66 | D-CCE | E VSALEKE VSALEKK NSALEKE VSALEKE VSALEK * |
| SEQ ID NO: 67 | D-CCK | K VSALKEK VSALKEK VSANKEK VSALKEK VSALKE * |
| SEQ ID NO: 68 | VSAL E4 | E VSALEKE VSALEKE VSALEKE VSALEK |
| SEQ ID NO: 69 | VSAL K4 | K VSALKEK VSALKEK VSALKEK VSALKE |
| SEQ ID NO: 70 | D-VSAL E4 | E VSALEKE VSALEKE VSALEKE VSALEK * |
| SEQ ID NO: 71 | D-VSAL-K4 | K VSALKEK VSALKEK VSALKEK VSALKE * |
| SEQ ID NO: 72 | VAAL E3 | E VAALEKE VAALEKE VAALEK |
| SEQ ID NO: 73 | VAAL K3 | K VAALKEK VSALKEK VSALKE |
| SEQ ID NO: 74 | D-VAAL E3 | E VAALEKE VAALEKE VAALEK * |
| SEQ ID NO: 75 | D-VAAL K3 | K VAALKEK VSALKEK VSALKE * |
| SEQ ID NO: 76 | ISAL E3 | E ISALEKE ISALEKE ISALEK |
| SEQ ID NO: 77 | ISAL K3 | K ISALKEK ISALKEK ISALKE |
| SEQ ID NO: 78 | D- ISAL E3 | E ISALEKE ISALEKE ISALEK * |
| SEQ ID NO: 79 | D- ISAL K4 | K ISALKEK ISALKEK ISALKE * |
| SEQ ID NO: 80 | IAAL E3 | E IAALEKE IAALEKE IAALEK |
| SEQ ID NO: 81 | IAAL K3 | K IAALKEK ISALKEK ISALKE |
| SEQ ID NO: 82 | D-IAAL E3 | E IAALEKE IAALEKE IAALEK * |
| SEQ ID NO: 83 | D-IAAL K3 | K IAALKEK ISALKEK ISALKE * | ii) Conjugate Comprising Albumin and One or More Oligomerization Moieties

Disclosed herein are conjugatees comprising albumin and one or more oligomerization moieties.

In an aspect, a disclosed conjugate further comprises a detectable label. Detectable labels are known to the art and include, but are not limited to: rhodamine, FITC, Cy3, Cy3.5, Cy5, Texas Red, Alexa Fluor 488, Alexa Fluor 610, Alexa Fluor 647, and Alexa Fluor 750.

(a) Albumin

Disclosed are conjugates comprising albumin. In some aspects, albumin can be natural or synthetic. In some aspects, albumin can be wild type albumin, an albumin variant, or a derivative of albumin. Albumin can be any of those albumins disclosed in EP Publication No. EP2556087, which is hereby incorporated by reference herein for its teaching of the same.

In some aspects, albumin can be human serum albumin (HSA). HSA has been used as a carrier in numerous drug delivery systems since it is inert, biodegradable, easily available, and significantly taken up by tumor and inflamed tissue. Conjugates comprising albumin can be prepared by chemical conjugation, direct genetic fusion, nanoparticle encapsulation and non-covalent association with albumin. HSA is a (non-glycosylated) soluble protein (mol. wt. 66,500); it constitutes about half of the serum proteins (35-50 g/L human serum). It can be synthesized by liver hepatocytes as a precursor protein (609 amino acid residues); the first 24 residues are cleaved after translation and HSA is secreted into the circulation. HSA is composed of 585 amino acid residues with 17 disulfide bridges and one free cysteine in position 34. It is a heart-shaped molecule with 67% of α-helices and no ß-sheets; it folds into three domains connected via long flexible loops. HSA is stable in the pH range of 4 to 9, soluble in 40% ethanol and is resistant to denaturation (stable at 60° C. up to 10 h). HSA has a serum half-life of 21 days. The FcRn receptor plays a key role in maintaining high levels of HSA in the circulation. FcRn prevents HSA from degradation by recycling the FcRn-HSA conjugate back from endosomes to the cell surface. The pH change from acidic to neutral triggers the release of the HSA ligand.

(b) Oligomerization Moiety

Oligomerization moieties can be any of those disclosed herein with regards to the conjugates comprising a targeting moiety and an oligomerization moiety. Thus, an oligomerization moiety can be any compound (e.g. oligopeptides, oligonucleotides, or oligosaccharides) that can bind or interact with at least one other oligomerization moiety to form a complex.

For example, in an aspect, an oligonucleotide can be a morpholino. Thus, disclosed is albumin comprising one or more grafted morpholinos. In an aspect, one or more morpholinos can comprise 1 morpholino, or 2 morpholinos, or 3 morpholinos, or 4 morpholinos, or 5 morpholinos, or 6 morpholinos, or 7 morpholinos, or 8 morpholinos, or 9 morpholinos, or 10 morpholinos. For example, in an aspect, a disclosed albumin can comprise 1 morpholino. In an aspect, a disclosed albumin can comprise 3 morpholinos. In an aspect, a disclosed albumin can comprise 10 morpholinos. In an aspect, a disclosed albumin can comprise 15 morpholinos. In an aspect, a disclosed albumin can comprise more than 10 grafted morpholinos. In an aspect, a disclosed albumin can comprise more than 15 grafted morpholinos. In an aspect, the one or more morpholinos can comprise one or more grafted MORF2 morpholinos. For example, a disclosed albumin-MORF2 conjugate can comprise 1 grafted morpholino. In an aspect, a disclosed albumin-MORF2 conjugate can comprise 3 grafted morpholinos. In an aspect, a disclosed albumin-MORF2 conjugate can comprise 10 grafted morpholinos. In an aspect, a disclosed albumin-MORF2 conjugate can comprise 15 grafted morpholinos. In an aspect, a disclosed albumin-MORF2 conjugate can comprise more than 15 grafted morpholinos. In an aspect, the one or more oligonucleotides can comprise the same oligonucleotides or can comprise differing oligonucleotides. In an aspect, the one or more morpholinos can comprise the same morpholinos or can comprise differing morpholinos. In an aspect, the one or more morpholinos or grafted morpholinos can have the same sequence. In an aspect, the one or more morpholinos can have different sequence. For example, in an aspect multiple morpholinos can be present, wherein the one or more morpholinos comprise different sequences or wherein the one or more morpholinos comprise the same sequence or a combination thereof.

iii) Kits

Disclosed herein are kits comprising a first conjugate comprising a targeting moiety and an oligomerization moiety, and a second conjugate comprising albumin and one or more oligomerization moieties. In an aspect, a disclosed kit can comprise instructions for administering a first conjugate comprising a targeting moiety and an oligomerization moiety and a second conjugate comprising albumin and one or more oligomerization moieties.

Disclosed herein are kits comprising a first conjugate comprising a targeting moiety and an oligonucleotide, and a second conjugate comprising albumin and one or more oligonucleotides. In an aspect, a disclosed kit can comprise instructions for administering a first conjugate comprising a targeting moiety and an oligonucleotide and a second conjugate comprising albumin and one or more oligonucleotides.

Disclosed herein are kits comprising a first conjugate comprising a targeting moiety and an oligopeptide, and a second conjugate comprising albumin and one or more oligopeptides. In an aspect, a disclosed kit can comprise instructions for administering a first conjugate comprising a targeting moiety and an oligopeptide and a second conjugate comprising albumin and one or more oligopeptides.

Disclosed herein are kits comprising a first conjugate comprising a targeting moiety and an oligomerization moiety, a second conjugate comprising albumin and one or more oligomerization moieties, and instructions for administering the first conjugate and the second conjugate.

Disclosed herein are kits comprising a first conjugate comprising a targeting moiety and an oligonucleotide, a second conjugate comprising albumin and one or more oligonucleotides, and instructions for administering the first conjugate and the second conjugate.

Disclosed herein are kits comprising a first conjugate comprising a targeting moiety and an oligopeptide, a second conjugate comprising albumin and one or more oligopeptides, and instructions for administering the first conjugate and the second conjugate.

In an aspect, the first conjugate and the second conjugate are co-formulated. In an aspect, the first conjugate and the second conjugate are co-packaged.

Disclosed are kits comprising those targeting moieties disclosed herein, oligomerization moieties disclosed herein, albumin disclosed herein, and/or conjugates comprising those targeting moieties, oligomerization moieties, or albumin disclosed herein.

iv) Pharmaceutical Compositions

Disclosed herein are pharmaceutical compositions comprising a disclosed composition comprising one or more conjugates disclosed herein. For example, in an aspect, disclosed pharmaceutical composition comprises (i) a conjugate comprising a targeting moiety and an oligomerization moiety and (ii) a pharmaceutically acceptable carrier. In an aspect, a disclosed pharmaceutical composition comprises (i) a conjugate comprising albumin and one or more oligomeriziation moieties and (ii) a pharmaceutically acceptable carrier. In an aspect, a disclosed pharmaceutical composition comprises (i) a first conjugate comprising a targeting moiety and an oligomerization moiety, (ii) a second conjugate comprising albumin and one or more oligomerization moieties, and (iii) a pharmaceutically acceptable carrier. Also disclosed are pharmaceutical compositions comprising (i) a conjugate comprising a targeting moiety and an oligonucleotide and (ii) a pharmaceutically acceptable carrier. In an aspect, a disclosed pharmaceutical composition comprises (i) a conjugate comprising albumin and one or more oligonucleotides and (ii) a pharmaceutically acceptable carrier. In an aspect, a disclosed pharmaceutical composition comprises (i) a first conjugate comprising a targeting moiety and an oligonucleotide, (ii) a second conjugate comprising albumin and one or more oligonucleotides, and (iii) a pharmaceutically acceptable carrier. In some aspects, the kits can comprise individual conjugates or mixtures of one or more conjugates.

Also disclosed are pharmaceutical compositions comprising (i) a conjugate comprising a targeting moiety and an oligopeptide and (ii) a pharmaceutically acceptable carrier. In an aspect, a disclosed pharmaceutical composition comprises (i) a conjugate comprising albumin and one or more oligopeptides and (ii) a pharmaceutically acceptable carrier. In an aspect, a disclosed pharmaceutical composition comprises (i) a first conjugate comprising a targeting moiety and an oligopeptide, (ii) a second conjugate comprising albumin and one or more oligopeptides, and (iii) a pharmaceutically acceptable carrier. In some aspects, the kits can comprise individual conjugates or mixtures of one or more conjugates.

In an aspect, a disclosed pharmaceutical composition can be administered to a subject in need of treatment of a B-cell malignancy, an inflammatory disorder, or an autoimmune disease with B cell involvement. For example, in an aspect, a disclosed pharmaceutical composition can be administered to a subject in need of treatment of a NHL. In an aspect, a disclosed pharmaceutical composition can be administered to a subject in need of treatment of one or more of the following: rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a disclosed pharmaceutical composition can be administered to a subject in need of treatment following receipt of a transplanted organ. In an aspect, a disclosed pharmaceutical composition can be administered to a subject in need of treatment, wherein the subject has JC virus.

The pharmaceutical carrier employed can be, for example, a solid, liquid, or gas.

Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Tablets and capsules are the preferred oral dosage units whereby solid pharmaceutical carriers are employed. Optionally, tablets can be coated by standard aqueous or nonaqueous techniques. A tablet containing a composition or conjugate disclosed herein can be prepared by compression or molding, optionally with one or more accessory ingredients or adjuvants. Compressed tablets can be prepared by compressing, in a suitable machine, a disclosed conjugate of composition in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

It is understood that the disclosed compositions can be prepared from the disclosed compounds. It is also understood that the disclosed compositions can be employed in the disclosed methods of using.

C. Methods i) Method of Inducing Apoptosis

Disclosed herein are methods of inducing apoptosis, comprising contacting a population of cells with a first conjugate comprising a targeting moiety and an oligomerization moiety; contacting a population of cells with a second conjugate comprising albumin and one or more oligomerization moieties; wherein the contacting of the cells with the first conjugate and the second conjugate induces apoptosis of the cells. In an aspect, a disclosed method can comprise repeating contacting a population of cells with a first conjugate comprising a targeting moiety and an oligomerization moiety. In an aspect, a disclosed method can comprise repeating contacting a population of cells with a second conjugate comprising albumin and one or more oligomerization moieties. In an aspect, a disclosed method can comprise contacting a population of cells with a first conjugate comprising a targeting moiety and an oligomerization moiety and contacting a population of cells with a second conjugate comprising albumin and one or more oligomerization moieties. In an aspect, a disclosed method can comprise contacting a population of cells with a first conjugate comprising a targeting moiety and an oligomerization moiety and contacting a population of cells with a second conjugate comprising albumin and one or more oligomerization moieties, wherein the first and second conjugates are premixed prior to contacting the population of cells.

Disclosed herein are methods of inducing apoptosis, comprising contacting a population of cells with a first conjugate comprising a targeting moiety and an oligonucleotide; contacting a population of cells with a second conjugate comprising albumin and one or more oligonucleotides; wherein the contacting of the cells with the first conjugate and the second conjugate induces apoptosis of the cells. In an aspect, a disclosed method can comprise repeating contacting a population of cells with a first conjugate comprising a targeting moiety and an oligonucleotide. In an aspect, a disclosed method can comprise repeating contacting a population of cells with a second conjugate comprising albumin and one or more oligonucleotides. In an aspect, a disclosed method can comprise contacting a population of cells with a first conjugate comprising a targeting moiety and an oligonucleotide and contacting a population of cells with a second conjugate comprising albumin and one or more oligonucleotides. In an aspect, a disclosed method can comprise contacting a population of cells with a first conjugate comprising a targeting moiety and an oligomerization moiety and contacting a population of cells with a second conjugate comprising albumin and one or more oligomerization moieties, wherein the first and second conjugates are premixed prior to contacting the population of cells.

Disclosed herein are methods of inducing apoptosis, comprising contacting a population of cells with a first conjugate comprising a targeting moiety and an oligopeptide; contacting a population of cells with a second conjugate comprising albumin and one or more oligopeptides; wherein the contacting of the cells with the first conjugate and the second conjugate induces apoptosis of the cells. In an aspect, a disclosed method can comprise repeating contacting a population of cells with a first conjugate comprising a targeting moiety and an oligopeptide. In an aspect, a disclosed method can comprise repeating contacting a population of cells with a second conjugate comprising albumin and one or more oligopeptides. In an aspect, a disclosed method can comprise contacting a population of cells with a first conjugate comprising a targeting moiety and an oligopeptide and contacting a population of cells with a second conjugate comprising albumin and one or more oligopeptides. In an aspect, a disclosed method can comprise contacting a population of cells with a first conjugate comprising a targeting moiety and an oligomerization moiety and contacting a population of cells with a second conjugate comprising albumin and one or more oligomerization moieties, wherein the first and second conjugates are premixed prior to contacting the population of cells.

In an aspect, the skilled person can determine an efficacious dose, an efficacious schedule, or an efficacious route of administration for a disclosed composition or a disclosed conjugate so as to induce apoptosis.

In an aspect, a disclosed method of inducing apoptosis can comprise confirming apoptosis of the cells. Methods of confirming apoptosis are known to the art and include, but are not limited to: measuring caspase-3 activity, measuring annexin V/propidium iodine binding, and measuring terminal deoxynucleotidyl transferase dUTP nick end-labeling. In an aspect, confirming apoptosis can comprise one of the following: measuring caspase-3 activity, measuring annexin V/propidium iodine binding, and measuring terminal deoxynucleotidyl transferase dUTP nick end-labeling. In an aspect, confirming apoptosis can comprise two of the following: measuring caspase-3 activity, measuring annexin V/propidium iodine binding, and measuring terminal deoxynucleotidyl transferase dUTP nick end-labeling. In an aspect, confirming apoptosis can comprise all of the following: measuring caspase-3 activity, measuring annexin V/propidium iodine binding, and measuring terminal deoxynucleotidyl transferase dUTP nick end labeling.

In an aspect of a disclosed method of inducing apoptosis, the population of cells can be B cells. In an aspect, B cells can be normal B cells. In an aspect, cells can be malignant B cells. In an aspect, the population of cells can be in a subject. In an aspect, B cells can be in a subject. In an aspect, a subject can have non-Hodgkin's lymphoma. In an aspect, a subject can have received an organ transplant. In an aspect, a subject can have JC virus. In an aspect, a subject can have rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy.

In an aspect of a disclosed method of inducing apoptosis, a targeting moiety can be specific for a non-internalizing cell surface molecule or slowly internalizing cell surface molecule. Examples of a non-internalizing cell surface molecule or a slowly internalizing cell surface molecule are known to the art. In an aspect, a non-internalizing cell surface molecule or slowly internalizing cell surface molecule can be on a cell or a population of cells. In an aspect, a cell or a population of cells can be B cells. In an aspect, the B cells can be normal B cells. In an aspect, the B cells can be malignant B cells.

In an aspect of a disclosed method of inducing apoptosis, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18 (TNFRSF18). In an aspect, a receptor can be a TNF-like weak inducer of apoptosis receptor (TWEAK or TNFSF12).

In an aspect of a disclosed method, a targeting moiety can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamer. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PR0131921, BCD-020, IBI-301, ublituximab, and BLX-301. In an aspect, the anti-CD20 receptor antibody can be 1F5.

In an aspect of a disclosed method of inducing apoptosis, albumin can be natural or synthetic. In some aspects, albumin can be wild type albumin, an albumin variant, or a derivative of albumin. Albumin can be any of those albumins disclosed in EP Publication No. EP2556087, hereby incorporated by reference herein. In some aspects, albumin can be HSA or a variant or derivative thereof.

Any of the conjugates disclosed herein can be used in the methods of inducing apoptosis. For example, disclosed herein are methods of inducing apoptosis, comprising contacting a population of cells with a first conjugate comprising a targeting moiety and an oligonucleotide; contacting a population of cells with a second conjugate comprising albumin and one or more oligonucleotides; wherein the contacting of the cells with the first conjugate and the second conjugate induces apoptosis of the cells. In an aspect, a disclosed method can comprise repeating contacting a population of cells with a first conjugate comprising a targeting moiety and an oligonucleotide. In an aspect, a disclosed method can comprise repeating contacting a population of cells with a second conjugate comprising albumin and one or more oligonucleotides. In an aspect, a disclosed method can comprise contacting a population of cells with a first conjugate comprising a targeting moiety and an oligonucleotide and contacting a population of cells with a second conjugate comprising albumin and one or more oligonucleotides. The disclosed conjugates comprising a targeting moiety and an oligonucleotide and conjugates comprising albumin and one or more oligonucleotides disclosed herein can be used.

Also disclosed herein are methods of inducing apoptosis, comprising contacting a population of cells with a first conjugate comprising a targeting moiety and an oligopeptide; contacting a population of cells with a second conjugate comprising albumin and one or more oligopeptides; wherein the contacting of the cells with the first conjugate and the second conjugate induces apoptosis of the cells. In an aspect, a disclosed method can comprise repeating contacting a population of cells with a first conjugate comprising a targeting moiety and an oligopeptide. In an aspect, a disclosed method can comprise repeating contacting a population of cells with a second conjugate comprising albumin and one or more oligopeptides. In an aspect, a disclosed method can comprise contacting a population of cells with a first conjugate comprising a targeting moiety and an oligopeptide and contacting a population of cells with a second conjugate comprising albumin and one or more oligopeptides. The disclosed conjugates comprising a targeting moiety and an oligopeptide and conjugates comprising albumin and one or more oligopeptides disclosed herein can be used. In an aspect, a disclosed method can comprise contacting a population of cells with a first conjugate comprising a targeting moiety and an oligomerization moiety and contacting a population of cells with a second conjugate comprising albumin and one or more oligomerization moieties, wherein the first and second conjugates are premixed prior to contacting the population of cells.

ii) Method of Inducing Apoptosis

Disclosed herein are methods of inducing apoptosis, comprising contacting a population of cells with a composition comprising a first conjugate comprising a targeting moiety and an oligomerization moiety and a second conjugate comprising a conjugate comprising albumin and one or more oligomerization moieties, wherein the contacting of the cells with the composition induces apoptosis of the cells. In an aspect, a disclosed method can comprise contacting a population of cells with a first conjugate comprising a targeting moiety and an oligomerization moiety and contacting a population of cells with a second conjugate comprising albumin and one or more oligomerization moieties, wherein the first and second conjugates are premixed prior to contacting the population of cells.

Disclosed herein are methods of inducing apoptosis, comprising contacting a population of cells with a composition comprising a first conjugate comprising a targeting moiety and an oligonucleotide and a second conjugate comprising a conjugate comprising albumin and one or more oligonucleotides, wherein the contacting of the cells with the composition induces apoptosis of the cells. Any of the disclosed conjugates comprising a targeting moiety and an oligonucleotide and/or albumin and one or more oligonucleotides can be used in the disclosed methods.

Disclosed herein are methods of inducing apoptosis, comprising contacting a population of cells with a composition comprising a first conjugate comprising a targeting moiety and an oligopeptide and a second conjugate comprising a conjugate comprising albumin and one or more oligopeptides, wherein the contacting of the cells with the composition induces apoptosis of the cells. Any of the disclosed conjugates comprising a targeting moiety and an oligopeptide and/or albumin and one or more oligopeptides can be used in the disclosed methods.

In an aspect of a disclosed method of inducing apoptosis, the method can comprise repeating the contacting of the cells with the composition. A disclosed method can comprise confirming apoptosis of the cells. Methods of confirming apoptosis are known to the art and include, but are not limited to: measuring caspase-3 activity, measuring annexin V/propidium iodine binding, and measuring terminal deoxynucleotidyl transferase dUTP nick end-labeling. In an aspect, confirming apoptosis can comprise one of the following: measuring caspase-3 activity, measuring annexin V/propidium iodine binding, and measuring terminal deoxynucleotidyl transferase dUTP nick end-labeling. In an aspect, confirming apoptosis can comprise two of the following: measuring caspase-3 activity, measuring annexin V/propidium iodine binding, and measuring terminal deoxynucleotidyl transferase dUTP nick end-labeling. In an aspect, confirming apoptosis can comprise all of the following: measuring caspase-3 activity, measuring annexin V/propidium iodine binding, and measuring terminal deoxynucleotidyl transferase dUTP nick end-labeling. In an aspect, the skilled person can determine an efficacious dose, an efficacious schedule, or an efficacious route of administration for a disclosed composition or a disclosed conjugate so as to induce apoptosis.

In an aspect of a disclosed method of inducing apoptosis, the population of cells can be B cells. In an aspect, B cells can be normal B cells. In an aspect, cells can be malignant B cells. In an aspect, the population of cells can be in a subject. In an aspect, B cells can be in a subject. In an aspect, a subject can have non-Hodgkin's lymphoma. In an aspect, a subject can have received an organ transplant. In an aspect, a subject can have JC virus. In an aspect, a subject can have rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy.

In an aspect, a disclosed methods can comprise contacting a population of cells with a first conjugate comprising a targeting moiety and an oligomerization moiety and contacting a population of cells with a second conjugate comprising albumin and one or more oligomerization moieties, wherein the first and second conjugates are premixed prior to contacting the population of cells.

iii) Method of Treatment

Disclosed herein are methods of treatment of a subject in need thereof, the method comprising administering to a subject a first composition comprising a first conjugate comprising a targeting moiety and an oligomerization moiety; and administering to the subject a second composition comprising a second conjugate comprising albumin and one or more oligomerization moieties, wherein the administering of the first composition and the second composition induces apoptosis of a targeted population of cells in the subject.

Disclosed herein are methods of treatment of a subject in need thereof, the method comprising administering to a subject a first composition comprising a first conjugate comprising a targeting moiety and an oligonucleotide; and administering to the subject a second composition comprising a second conjugate comprising a copolymer carrier and one or more oligonucleotides, wherein the administering of the first composition and the second composition induces apoptosis of a targeted population of cells in the subject. Any of the disclosed conjugates comprising a targeting moiety and an oligonucleotide and/or albumin and one or more oligonucleotides can be used in the disclosed methods.

Disclosed herein are methods of treatment of a subject in need thereof, the method comprising administering to a subject a first composition comprising a first conjugate comprising a targeting moiety and an oligopeptide; and administering to the subject a second composition comprising a second conjugate comprising albumin and one or more oligopeptides, wherein the administering of the first composition and the second composition induces apoptosis of a targeted population of cells in the subject. Any of the disclosed conjugates comprising a targeting moiety and an oligopeptide and/or albumin and one or more oligopeptides can be used in the disclosed methods.

In an aspect, administering comprises intravenous administration. In an aspect, a disclosed method can comprise repeating the administration of the first composition. In an aspect, a disclosed method can comprise repeating the administration of the second composition. In an aspect, a disclosed method can comprise repeating the administration of the first composition and repeating the administration of the second composition. In an aspect, a disclosed method can comprise confirming apoptosis of the targeted population of cells. In an aspect, the skilled person can determine an efficacious dose, an efficacious schedule, or an efficacious route of administration for a disclosed composition or a disclosed conjugate so as to treat a subject in need thereof.

In an aspect of a disclosed method of treatment, the induction of apoptosis can be detected by methods known to the art and also disclosed herein. In an aspect, cells undergoing apoptosis or being targeted by the method of treatment can be those cells disclosed herein. In an aspect, a subject can be those subjects disclosed herein.

In an aspect, the first conjugate and second conjugate can be administered consecutively. For example, there can be a lag period of 1, 2, 3, 4, 5, 6, 7, 8, 9, 10, 11, 12, 13, 14, 15, 16, 17, 18, 19, 20, 21, 22, 23, or 24 hours between administering the first conjugate and administering the second conjugate. In some aspects, there can be a lag period of 1, 2, 3, 4, 5, 6, or 7 days between administering the first conjugate and administering the second conjugate. In an aspect, the first conjugate and second conjugate can be administered simultaneously. Simultaneous administration can include administering the first conjugate and second conjugate as separate compositions but at the same time or premixing the first conjugate and second conjugate as one single composition.

D. Synthesis i) Synthesis of Conjugate Comprising a Targeting Moiety and an Oligonucleotide Disclosed herein are processes of synthesizing a conjugate comprising a targeting moiety and an oligonucleotide, the process comprising obtaining a targeting moiety, modifying an oligonucleotide, and conjugating the targeting moiety with the oligonucleotide. In an aspect, a targeting moiety can be conjugated to the oligonucleotide via a thioether bond. In an aspect, an oligonucleotide can be SMCC modified. In an aspect, the oligonucleotide can contain a 3'-maleimido group. In an aspect, a disclosed process of synthesizing a conjugate can comprise introducing a detectable label. In an aspect of a disclosed process of synthesizing a conjugate, a targeting moiety can be a disclosed targeting moiety. For example, a targeting moiety can be a Fab' fragment specific for CD20. In an aspect of a disclosed process of synthesizing a conjugate, an oligonucleotide can be a disclosed oligonucleotide. For example, a disclosed oligonucleotide can be a morpholino comprising 10 bp-40 bp.

ii) Synthesis of Conjugate Comprising a Targeting Moiety and an Oligonucleotide

Disclosed herein are processes of synthesizing a conjugate comprising a targeting moiety and an oligopeptide, the process comprising obtaining a targeting moiety, modifying an oligopeptide, and conjugating the targeting moiety with the oligopeptide. In some aspects, a targeting moiety can be an Fab' fragment.

The Fab' fragment can be prepared from the whole antibody by enzyme digestion into $F(ab')_2$ and reduction into Fab' and purification on a chromatographic column. Alternatively, the Fab' fragment can be synthesized by genetic engineering by inserting a relevant plasmid into bacteria. An oligopeptide can be preferably synthesized by solid phase peptide synthesis. At the amino end of the oligopeptide a short spacer starting with cysteine (for example CYGG) can be introduced. Incubation of the Fab' with the modified oligopeptide results in Fab'-oligopeptide conjugate where the components are bound via a thioether bond.

iii) Synthesis of Conjugate Comprising Albumin and One or More Oligonucleotides

Disclosed herein are processes of synthesizing a conjugate comprising albumin and one or more oligonucleotides, the process comprising: obtaining albumin, modifying one or more oligonucleotides, and conjugating the albumin to one or more oligonucleotides. In an aspect, a disclosed process of synthesizing a conjugate can comprise introducing a detectable label. In an aspect of a disclosed process of synthesizing a conjugate, one or more oligonucleotides can be one or more disclosed oligonucleotides. For example, one or more disclosed oligonucleotides can be morpholinos each comprising 10 bp-40 bp.

iv) Synthesis of Conjugate Comprising Albumin and One or More Oligopeptides

Disclosed herein are processes of synthesizing a conjugate comprising albumin and one or more oligopeptides, the process comprising: obtaining albumin, modifying one or more oligopeptides, and conjugating the albumin to one or more oligopeptides. In an aspect, a disclosed process of synthesizing a conjugate can comprise introducing a detectable label. In an aspect of a disclosed process of synthesizing a conjugate, one or more oligopeptides can be one or more disclosed oligopeptides. For example, one or more disclosed oligonucleotides can be coiled coil forming peptides.

v) Synthesis of Composition Comprising Conjugate Comprising a Targeting Moiety and an Oligonucleotide and Conjugate Comprising an Albumin Carrier and One or More Oligonucleotides Disclosed herein are processes of synthesizing a conjugate comprising a targeting moiety and an oligonucleotide and a conjugate comprising albumin and one or more oligonucleotides, the process comprising contacting a first conjugate comprising a targeting moiety and an oligonucleotide with a second conjugate comprising albumin to one or more oligonucleotides. In an aspect, an oligonucleotide of a first conjugate hybridizes to the one or more oligonucleotides of a second conjugate. In an aspect, a disclosed process can comprise generating a first conjugate. In an aspect, a disclosed process can comprise generating a second conjugate. In an aspect, a disclosed process can comprise generating a first conjugate and generating a second conjugate. In an aspect, a first conjugate can be any disclosed conjugate comprising a targeting moiety and an oligonucleotide. In an aspect, a second conjugate can be any disclosed conjugate comprising albumin and one or more oligonucleotides. For example, in an aspect of a disclosed process, a targeting moiety can be a Fab' fragment specific for CD20, albumin can be natural albumin, synthetic albumin, or an albumin derivative, and each of the oligonucleotides can be a morpholinos comprising 10 bp-40 bp, wherein the morpholino of the first conjugate is complementary to the one or more morpholinos of the second conjugate.

vi) Synthesis of Composition Comprising Conjugate Comprising a Targeting Moiety and an Oligonucleotide and Conjugate Comprising an Albumin Carrier and One or More Oligonucleotides Disclosed herein are processes of synthesizing a conjugate comprising a targeting moiety and an oligopeptide and a conjugate comprising albumin and one or more oligopeptides, the process comprising contacting a first conjugate comprising a targeting moiety and an oligopeptide with a second conjugate comprising albumin to one or more oligopeptides. In an aspect, an oligopeptide of a first conjugate hybridizes to the one or more oligopeptides of a second conjugate. In an aspect, a disclosed process can comprise generating a first conjugate. In an aspect, a disclosed process can comprise generating a second conjugate. In an aspect, a disclosed process can comprise generating a first conjugate and generating a second conjugate. In an aspect, a first conjugate can be any disclosed conjugate comprising a targeting moiety and an oligopeptide. In an aspect, a second conjugate can be any disclosed conjugate comprising albumin and one or more oligopeptides. For example, in an aspect of a disclosed process, a targeting moiety can be a Fab' fragment specific for CD20, albumin can be natural albumin, synthetic albumin, or an albumin derivative, and each of the oligopeptides can be coiled coil forming peptides, wherein the coiled coil forming peptide of the first conjugate is complementary to the one or more coiled coil forming peptides of the second conjugate.

It is contemplated that each disclosed methods can further comprise additional steps, manipulations, and/or components. It is also contemplated that any one or more step, manipulation, and/or component can be optionally omitted. It is understood that disclosed methods can be used to provide the disclosed compounds. It is also understood that the products of the disclosed methods can be employed in the disclosed methods of using.

E. Examples

The following examples are put forth so as to provide those of ordinary skill in the art with a description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention. Efforts have been made to ensure accuracy with respect to numbers (e.g., amounts, temperature, etc.), but some errors and deviations should be accounted for.

(1) HSA as the Backbone of a Nanoconjugate

HSA has been used as a carrier in numerous drug delivery systems since it is inert, biodegradable, easily available, and significantly taken up by tumor and inflamed tissue. Albumin containing drug delivery systems can be prepared by chemical conjugation, direct genetic fusion, nanoparticle encapsulation and non-covalent association with albumin. FDA approved albumin products include antidiabetic fusion products Levemir® and Victoza®, nanoparticle formulation of paclitaxel Abraxane®, and diagnostic products Nanocoll® and Albures®. Other experimental applications targeted the —SH group of cysteine-34 of HSA. HSA is a robust protein that can be chemically modified without denaturation.

Several studies have demonstrated the mechanism of action of Abraxane®. It dissolves rapidly following intravenous infusion resulting in paclitaxel complexes similar in size to albumin or water-soluble polymer-drug conjugates. In solid tumors the conjugatees extravasate due to the EPR (enhanced permeability and retention) effect and further uptake of complexes is mediated by the gp60 transcytosis pathway and subsequent binding to SPARC (secreted protein, acidic, and rich in cysteine).

Albumin provides several advantages to the disclosed nanoconjugates such as i) long intravascular half-life of the biocompatible nanoconjugate which can improve efficacy and decrease the number of doses needed; ii) albumin is a natural macromolecule easy to obtain; iii) it has a scalable synthesis of albumin-based conjugates in GMP environment; iv) the treatment protocol is a two-component system suitable for the development of efficient pre-targeting strategies; and v) it has an absence of low molecular weight cytotoxic drugs.

Hybridization of two complementary morpholino oligonucleotides or association of complementary coiled-coil forming peptides at B cell surface mediates crosslinking of CD20 receptors and initiates apoptosis. One oligonucleotide (MORF1) or coiled-coil forming peptide (CCE) is bound to an antibody fragment recognized by the CD20 receptor (nanoconjugate 1; Fab'-motif1); the complementary oligonucleotide (MORF2) or oligopeptide (CCK) is bound in multiple copies to human serum albumin (nanoconjugate 2; HSA-motif2). Thus the new paradigm in macromolecular therapeutics is composed of two nanoconjugates, for example: a) Fab'-MORF1+HSA-(MORF2)x; b) Fab'-CCE+HSA-(CCK)x. The preferable administration of conjugates is consecutive. The first conjugate (e.g. Fab'-MORF1) is administered intravenously. After a time lag for 5 h (this is optimal for SCID mice) the second nanoconjugate can be administered (also intravenously). Alternatively, nanoconjugates could be premixed before administration and applied in one dose.

However, the proposed two-step approach, i.e., consecutive administration of Fab'-MORF1 (or Fab'-CCE) followed by HSA-(MORF2)$_x$ (or HSA-(CCK)$_y$), offers the opportunity of pre-targeting [1-4]. The pre-targeting strategy is commonly used in cancer radioimmunotherapy. The purpose is to achieve desirable pharmacokinetic goals by separating therapeutic modalities (e.g., radionuclides) from targeting functionality (e.g., antibodies) [5]. Over the years, the concept of pre-targeting has been expanded and applied for such strategies as amplified therapeutic delivery [6] and universal targeting of different tumor ligands [7]. These approaches aim to improve therapeutic efficacies and reduce adverse side reactions [8]. Similarly, for drug-free macromolecular therapeutics, the Fab' conjugates can be used as a pre-targeting agent, and then the multivalent albumin conjugates are delivered as the therapeutically active dose. The time lag between the two doses can be adjusted based on pharmacokinetics and biodistribution of the Fab' conjugates, in order to optimize pre-targeting efficiency and achieve maximum tumor-to-tissue accumulation in individual patients. We have recently proven this concept in mice.

(a) Synthesis and Characterization of Nanoconjugates (i) Nanoconjugate 1A-(Fab'-MORF1) Using Fab' from 1F5 Antibody Nanoconjugate 1A was prepared using the Fab' fragment from 1F5 Ab: First, 200 nmol MORF1-NH$_2$ (containing a 3'-primary amine) (Gene Tools, Philomath, Oreg.) was reacted with 0.67 mg (2 μmol) succinimidyl-4-(N-maleimidomethyl)cyclohexane-1-carboxylate (SMCC) (Soltec Ventures, Beverly, Mass.) in 170 μL DMSO to produce the MORF1-mal (containing a 3'-maleimide). The reaction was performed at RT (room temperature) for 24 h. The product was isolated by precipitation into 1.5 mL acetone, purified by dissolution-precipitation in deionized water-acetone twice, and dried under vacuum. Second, 200 nmol MORF1-mal was dissolved in 200 μL 10 mM PBS (pH 6.5), and then the solution was mixed with 200 nmol (~10 mg) freshly reduced Fab'-SH in 2 mL PBS (pH 6.5). The reaction was performed at 4° C. for 24 h. Finally, the Fab'$_{1F5}$-MORF1 conjugate was purified using size exclusion chromatography (SEC) to remove free, unconjugated Fab'$_{1F5}$ and MORF1. An ÄKTA FPLC system (GE Healthcare, Piscataway, N.J.) equipped with Sephacryl S-100 HR16/60 column (GE Healthcare) eluted with PBS (pH 7.2) was used. Optionally, Fab'$_{1F5}$-MORF1 was labeled with 5-10 molar excess Rhodamine Red™-X succinimidyl ester (R6010) (Molecular Probes®, Invitrogen, Carlsbad, Calif.) for imaging studies. The product was purified using a PD-10 desalting column (GE Healthcare). To determine Fab'$_{1F5}$ equivalent concentration of the Fab'$_{1F5}$-MORF1 conjugate, a bicinchoninic acid (BCA) protein assay (Thermo Scientific Pierce, Rockford, Ill.) was used. The obtained values were compared to the MORF1 equivalent concentrations obtained from UV-visible spectroscopy (using a molar absorptivity of 278,000 $M^{-1}$ $cm^{-1}$). Such comparison confirmed a 1:1 stoichiometry of the coupling reaction.

(ii) Nanoconjugate 1B-(Fab'-MORF1) Using Fab' from Rituximab

Nanoconjugate 1B was prepared similarly to 1A. To a solution of 21 mg Rituximab 2.1 mg pepsin was added. The mixture was incubated at 37° C. for 85 min. Following separation of F(ab')$_2$ on a Sephacryl 100 60/100 column (S-100), 12 mg of F(ab')$_2$ was isolated. F(ab')$_2$ was reduced with TCEP to Fab' immediately before reacting with MORF1.

The Fab'$_{RTX}$-MORF1 conjugate was synthesized by reaction of freshly prepared Fab'$_{RTX}$-SH with 3'-maleimide MORF1 as described above. In brief, MORF1-mal (162 nmol; 1.4 mg) was reacted with Fab'$_{RTX}$-SH (80 nmol; 4 mg) in PBS, pH 6.5 at 4° C. for 20 h. The product was purified by ultrafiltration (30 kDa) with PBS five times (alternatively, it can be purified using S-100 column). The Fab'$_{RTX}$ concentration was determined by BCA assay using standard working curves. The ratio of Fab'$_{RTX}$/MORF1 is ~1/1.

(iii) Nanoconjugate 1C-(Fab'-CCE) Using Fab' from 1F5 Antibody

Nanoconjugate 1C (Fab'-CCE) conjugate was prepared using known techniques. The Fab' fragment of 1F5 was prepared as described above. Fab'-(CCE)$_1$ was obtained by conjugation of Fab' with CCE using maleimide-thiol chemistry. Immediately prior to use, F(ab')$_2$ was reduced to Fab' with 10 mM tris(2-carboxyethyl) phosphine hydrochloride (TCEP) in PBS (pH 7.4) containing 5 mM EDTA for 1 h at 37° C. in the dark. CCE (1.5× in excess to Fab') was added and the coupling reaction proceeded at 4° C. in the dark overnight. The crude product was then purified twice using a PD10 column. This coupling reaction follows a 1:1 stoichiometry. Thus the resulting conjugate was named Fab'-(CCE)$_1$.

The digestion and conjugation were confirmed by size exclusion chromatography (SEC), SDS-PAGE and RP-HPLC. 1F5 Ab, F(ab')$_2$, Fab' fragment, and Fab'-(CCE)$_1$ were individually injected into a SEC column and showed different characteristic elution times. SDS-PAGE demonstrated the successful digestion of 1F5 antibody and conjugation of Fab' fragment with CCE.

Fab' fragment from 1F5 Ab or from Rituximab were used as examples. This does not restrict the coverage to only these Abs; numerous Abs, such as ofatumumab, obinutuzumab, and tositumumab can be used.

(iv) Nanoconjugate 2A-HSA Grafted with Multiple Copies of MORF2-HSA-(MORF2)x Nanoconjugate 2A (HSA-(MORF2)x) was synthesized in two steps (FIG. 1). First, a fraction of HSA amino groups were converted to maleimido groups by the reaction with the N-hydroxysuccinimide ester of the heterobifunctional cross-linking agent SM-(PEG)$_x$ (succinimidyl-[(N-maleimidopropionamido)-diethyleneglycol] ester). In the second step, freshly prepared MORF2-SH was attached to HSA via thioether bond. For example, 5 mg HSA ([NH$_2$]: 778 nmol/mg HSA, 1 eq.) was dissolved in 400 µL PBS (pH 7.5) and mixed with 18.3 mg SM-(PEG)$_x$ (43 µmol, 11 eq) in 150 µL DMSO. The mixture was stirred at RT for 6 h and at 4° C. overnight. The excess SM-(PEG)$_x$ was removed by ultrafiltration (30,000 cu group determined by modified Ellman's assay was 318 nmol/mg HSA (41% conversion). 5.7 mg MORF2-SS-R was dissolved in 100 µL PBS (pH 7.0) and added into 900 µL TCEP solution (10 mM, in PBS pH 7.0), then incubated at RT for 2.5 h. After working up, excess TCEP was removed by ultrafiltration (3,000 cut-off) four times to yield MORF2-SH, final volume was 500 µL.

HSA-mal (2 mg; 670 nmol mal group, in 330 µL PBS, 1 eq.) mixed with MORF2-SH solution (670 nmol, 1 eq.) and incubated at RT for 2.5 h. After working up, free MORF2-SH was removed by ultrafiltration (3,000 Da cut-off) four times to yield HSA-(MORF2)$_x$, final volume was 850 µL. FPLC analysis showed that there was no free HSA. HSA-MORF2 (5 µL) was dissolved in 1 mL HCl (0.1 M), the OD at 264 nm was 0.351 (E=252,000). [MORF2] was 278 uM. The HSA concentration of HSA-(MORF2)x was determined by BCA assay with HSA standard working curve, [HSA]: 27.6 uM. The composition of the conjugate was HSA-(MORF2)$_{10}$ (see synthesis in FIG. 1).

(v) Nanoconjugate 2B-HSA Grafted with Multiple Copies of CCK-HSA-(CCK)x

Nanoconjugate 2B (HSA-(CCK)x) can be synthesized similarly to nanoconjugate 2A. HSA modified with SM-(PEG)$_2$ can be reacted with the CCK peptide (CYGG K VSALKEK VSALKEE VSANKEK VSALKEK VSALKE) via thioether bonds by the reaction of the maleimido groups on HSA with the SH group of the CCK peptide

(vi) Detection of Hybridization MORF1/MORF2 by UV-Visible Spectroscopy

Figure 2:
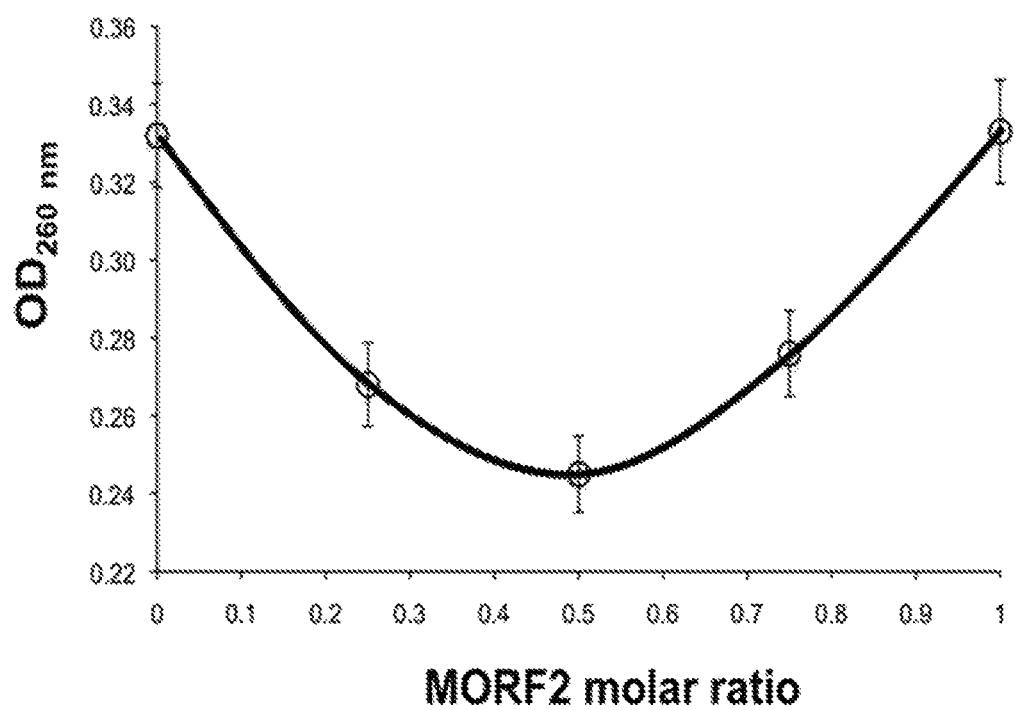
FIG. 2 shows the in vitro hybridization of Fab'-MORF1 and HSA-(MORF2)$_{10}$. The optical density (OD) at 260 nm decreased when the two conjugates were mixed in different ratios (pH 7.4; PBS). Maximal hypochromic effect (minimal UV absorbancy) was observed at 1:1 MORF1:MORF2 ratio.

Analysis of the hypochromic effect upon MORF1-MORF2 hybridization was performed using a Varian Cary 400 Bio UV-visible spectrophotometer (Agilent Technologies, Santa Clara, Calif.). MORF1 and MORF2 (or Fab'-MORF1 and HSA-MORF2) were firstly dissolved in 1 mL PBS pH=7.4 each at a concentration of 2.5 µM (MORF equivalent) and then mixed in different ratios at RT. The final concentrations of MORF oligos (MORF1+MORF2) in every solution mixture were kept constant (2.5 µM). For example, the mixture containing 75% MORF1 (or 25% MORF2) was done by mixing 0.75 mL of 2.5 µM MORF1 solution with 0.25 mL of 2.5 µM MORF2 solution. Samples were placed in a 1-cm quartz cuvette for measurement. The optical density (OD) at 260 nm (contributed by bases) was recorded. All measurements were performed in triplicate. In vitro hybridization of Fab'-MORF1 and HSA-(MORF2)$_{10}$ was analyzed by UV-Vis (FIG. 2).

(b) Apoptotic Assays

In vitro apoptosis induction of human Burkitt's B-cell non-Hodgkin's lymphoma (NHL) Raji cells by co-treatment with Fab'-MORF1 and HSA-MORF2 was evaluated by two assays: Annexin V/propidium iodide (PI) binding assay, and caspase-3 activation assay. In all experiments, 1F5 mAb hyper-crosslinked with a goat antimouse (GAM) secondary antibody (2° Ab) (KPL, Gaithersburg, Md.) was used as a positive control (molar ratio 1F5:GAM=2:1). Untreated cells (in culture media) were used as negative controls.

In vitro apoptosis induction of human Burkitt's B-cell non-Hodgkin's lymphoma (NHL) Raji cells by co-treatment with Fab'$_{RTX}$-MORF1 (or Fab'$_{1F5}$-MORF1) and HSA-(MORF2)x was evaluated by two assays: Annexin V/propidium iodide (PI) binding assay and TUNEL (terminal depxynucleotide mediated-dUTP nick-end labeling) assay. Two cell exposure protocols were used. Consecutive exposure: the cells were incubated with Fab'$_{RTX}$-MORF1 (or Fab'$_{1F5}$-MORF1) conjugate first. After 1 h the cells decorated with MORF1 were exposed to HSA-(MORF2)x for 24 h. Premixed exposure: The nanoconjugates Fab'$_{RTX}$-MORF1 (or Fab'$_{1F5}$-MORF1) and HSA-(MORF2)x were mixed at 37° C. and after 1 h Raji cell were exposed to a preformed, self-assemble multivalent conjugate for 24 h. In all experiments, Rituximab (RTX) or 1F5 mAb hyper-crosslinked with a goat antihuman (GAH)(Life Technologies™, MD) or goat antimouse (GAM) secondary antibody (2° Ab) (KPL, Gaithersburg, Md.) was used as a positive control (molar ratio RTX:GAH=2:1, 1F5:GAM=2:1). Non-treated cells (in culture media) were used as negative controls. The procedures of each assay are described below.

(i) Annexin V/PI Assay

Figure 3:
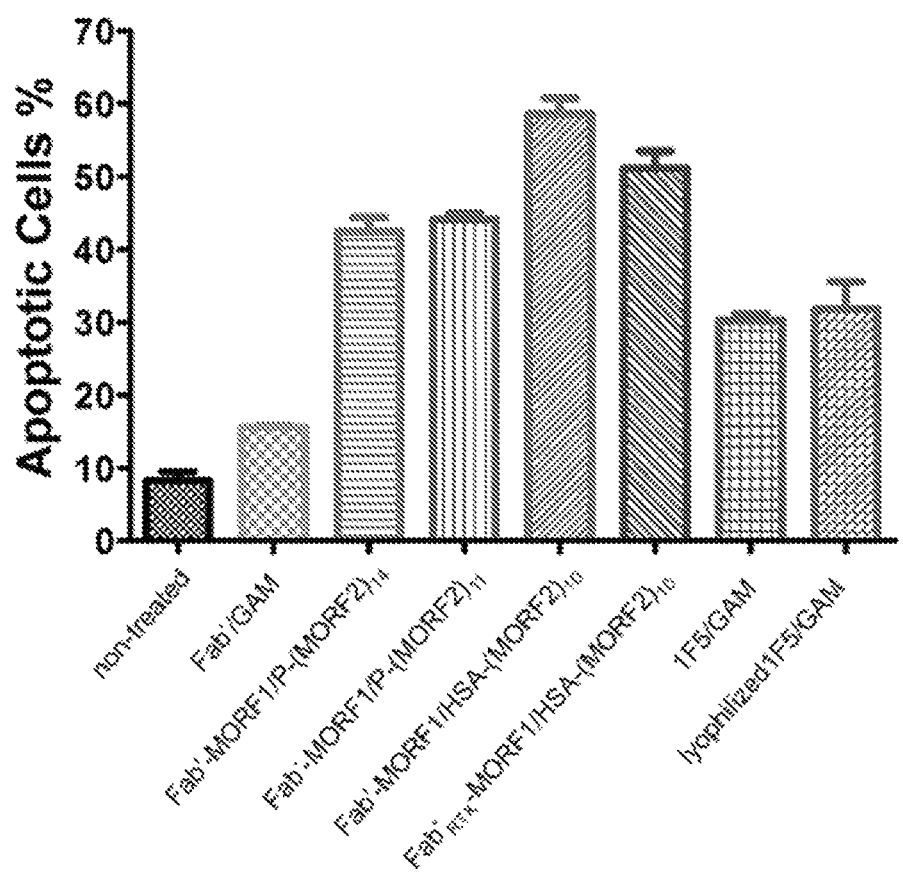
FIG. 3 shows apoptosis induction in Raji B cells. Percentage of apoptotic cells were analyzed by Annexin V/PI binding and quantified by flow cytometry. Incubation time was 24 h. Non-treated: cells in culture medium; Fab' goat anti-mouse (GAM): Fab' (1 µM) followed (1 h later) by goat anti-mouse (GAM) secondary Ab (0.5 µM); Fab'$_{1F5}$-MORF1/P-(MORF2)$_{14}$: Fab'$_{1F5}$-MORF1 (1 µM) and (1 h later) P-(MORF2)$_{14}$ (1 µM MORF2-eqv); Fab'$_{1F5}$-MORF1/P-(MORF2)$_{11}$: Fab'$_{1F5}$-MORF1 (1 µM) and (1 h later) P-(MORF2)$_{11}$ (1 µM MORF2-eqv); Fab'$_{1F5}$-MORF1/HSA-(MORF2)$_{10}$: Fab'$_{1F5}$-MORF1 (1 µM) and (1 h later) HSA-(MORF2)$_{10}$ (1 µM, MORF2-eqv); Fab'$_{RTX}$-MORF1 HSA-(MORF2)$_1$: Fab'$_{RTX}$-MORF1 and (1 h later) HSA-(MORF2)$_{10}$ (1 µM, MORF2-eqv); 1F5/GAM: 1F5 mAb (1 µM) followed (1 h later) by goat anti-mouse secondary Ab (0.5 µM); Lyophilized 1F5/GAM: lyophilized 1F5 was used. (Fab'$_{1F5}$:fragment of 1F5 antibody; Fab'$_{RTX}$: fragment of Rituximab antibody)
Figure 4:
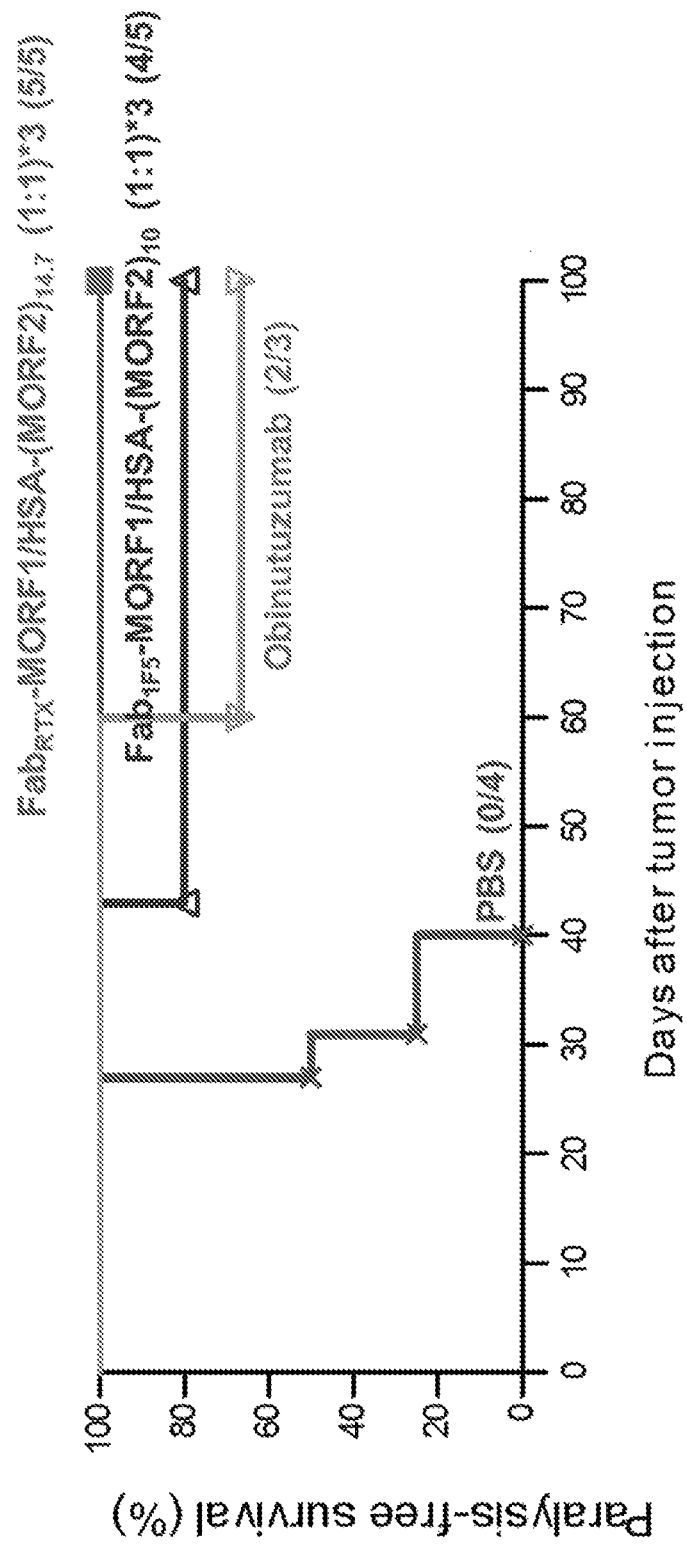
FIG. 4 shows the therapeutic efficacy against systemic lymphoma in SCID mice. Four million Raji-B cells were injected via tail vein on day 0; incidence of hind-limb paralysis or survival of mice was monitored until day 100. Three-dose treatment on days 1, 3 and 5. PBS, mice injected with PBS (n=4); Fab'$_{RTX}$-MORF1/HSA-(MORF2)$_{14.7}$, consecutive treatment of Fab'$_{RTX}$-MORF1 and 5 h later of HSA-(MORF2)$_{14.7}$, 3 doses (n=5; MORF1:MORF2=1:1); Fab'$_{1F5}$-MORF1/HSA-(MORF2)$_{10}$, consecutive treatment of Fab'$_{1F5}$-MORF1 and 5 h later of HSA-(MORF2)$_{10}$, 3 doses (n=5; MORF1:MORF2=1:1); obinutuzumab, single dose on day 1. The paralysis-free survival of mice is presented in a Kaplan-Meier plot. Numbers of long-term survivors in each group are indicated.

Results in FIG. 3 clearly show the high activity of HSA conjugates when compared to HPMA copolymer conjugates (P-conjugates). Both HSA conjugate combinations, a) Fab'$_{1F5}$-MORF1/HSA-(MORF2)$_{10}$ (Fab' from 1F5 antibody); b) Fab'$_{rtx}$-MORF1/HSA-(MORF2)$_{10}$ (Fab' from Rituximab antibody) possessed higher apoptosis levels than HPMA copolymer-based combinations, Fab'$_{1F5}$-MORF1/P-(MORF2)$_{14}$ and Fab'$_{1F}$5-MORF1/P-(MORF2)$_{11.4}$ (P is the HPMA copolymer backbone).

Annexin V-FITC and PI staining were performed following the RAPID™ protocol provided by the manufacturer (Oncogene Research Products, Boston, Mass.). For the consecutive treatment, 2×10$^5$ Raji cells were suspended in 0.4 mL fresh growth medium containing 1 µM Fab'$_{RTX}$-MORF1 (or Fab'$_{1F5}$-MORF1). The cells were incubated for 1 h in a humidified atmosphere at 37° C. with 5% CO$_2$, and then washed twice with PBS+1% bovine serum albumin (BSA), followed by resuspension in 0.4 mL medium containing 1 µM (MORF2-eqv.) of HSA-(MORF2)x. The cell suspension was incubation for 24 h. For the premixed treatment, first, 1 µM Fab'$_{1F5}$-MORF1 (or Fab'$_{RTX}$-MORF1) was mixed with 1 µM (MORF2-eqv.) HSA-(MORF2)x in culture medium at 37° C. for 1 h, and then 2×10$^5$ Raji cells were suspended in 0.4 mL of the premixed solution. The cell suspension was incubated for 24 h. For the positive control, cells were first incubated with 1 µM of 1F5 or RTX mAb in culture medium for 1 h, and then washed twice with PBS+ 1% BSA, followed by resuspension in 0.4 mL of fresh growth medium containing 0.5 µM GAM or GAH. The cells were incubated for another 24 h at 37° C. Prior to staining, cells were washed twice with PBS. All experiments were carried out in triplicate.

To evaluate different degrees of substitution of HSA-(MORF2)x on apoptosis induction, three substitutions of HSA-(MORF2)x conjugates were synthesized from different HSA-mal precursor (mal to HSA ratio is 20 or 30, respectively) with varying amounts of MORF2-SH to produce HSA-(MORF2)$_{6.3}$, HSA-(MORF2)$_{10}$ and HSA-(MORF2)$_{14.7}$.

A previous drug-free macromolecular therapeutics system was composed of two hybrid conjugates: (1) anti-CD20 Fab' linked to MORF1 (Fab'$_{1F5}$-MORF1, Fab' fragment was obtained from 1F5 mouse mAb), and (2) HPMA copolymer grafted with multiple copies of MORF2 (P-(MORF2)x). The Fab'$_{1F5}$-MORF1/P-(MORF2)x worked well. The dynamic and flexible nature of HPMA copolymer backbone allowed a conformational response to CD20 cross-linking. Albumin is the most abundant plasma protein with a molecular weight of 66.5 kDa. Human serum albumin is playing an increasing role as a versatile protein carrier for drug targeting and for improving the pharmacokinetics profile of peptide- or protein-based drugs. Unlike the flexibility of polymer backbone, HSA has an approximate three-dimensional shape due to protein folding. CD20 crosslinking and apoptosis induction was mediated by MORF1/MORF2 hybridization. The MORF1-MORF2 hybridization efficiency between HSA-(MORF2)x and Fab'-MORF1 may be affected by the intrinsic structure of HSA. Importantly, when comparing apoptotic levels achieved by incubating Raji cells with the HSA-based system and with the HPMA copolymer-based system, the apoptotic levels (determined using the Annexin V/PI assay) of the HSA-based system were considerable higher (shown in FIG. 3).

Figure 5:
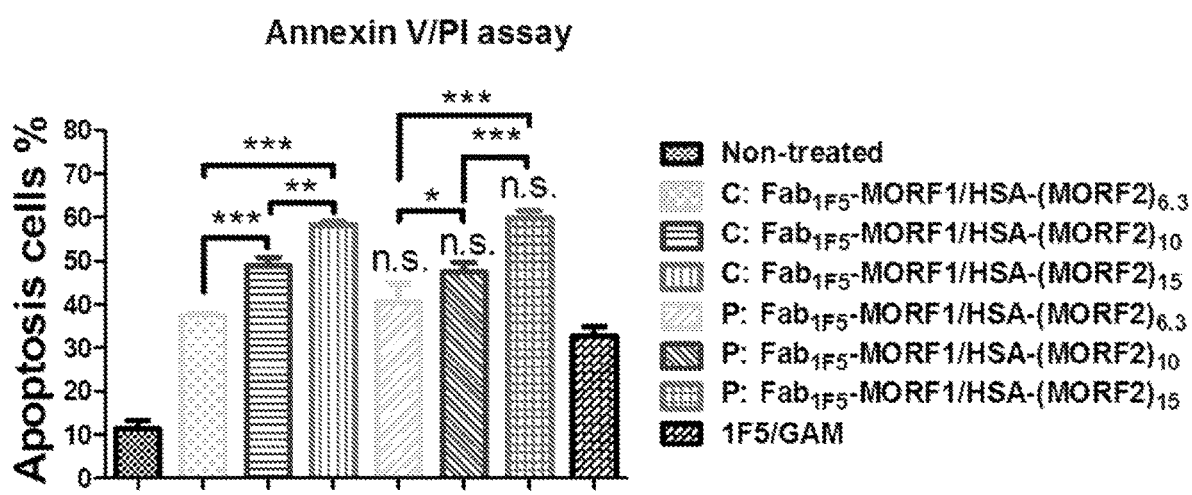
FIG. 5 shows the effect of the degrees of substitution of HSA-(MORF2)x (co-treatment with Fab1F5-MORF1) on apoptosis induction of Raji B-cells. Percentage of apoptotic cells was analyzed by Annexin V/PI binding and quantified by flow cytometry. Incubation time was 24 h. Non-treated, cells in culture medium; 1F5/GAM, 1F5 mAb (0.5 µM) followed (1 h later) by goat anti-mouse secondary Ab (0.25 µM); P: Fab'$_{1F5}$-MORF1/HSA-(MORF2)x, premixture of Fab'$_{1F5}$-MORF1 (1 µM) and HSA-(MORF2)x with different degrees of substitution (HSA-(MORF2)$_{6.3}$ or HSA-(MORF2)$_{10}$ or HSA-(MORF2)$_{14.7}$; 1 µM, MORF2-eqv). C: Fab'$_{1F5}$-MORF1/HSA-(MORF2)x, consecutive, Fab'$_{1F5}$-MORF1 (1 µM) followed (1 h later) by HSA-(MORF2)x with different degrees of substitution (HSA-(MORF2)$_{6.3}$ or HSA-(MORF2)$_{10}$ or HSA-(MORF2)$_{14.7}$; 1 µM, MORF2-eqv). Percentage of apoptotic cells was quantified by flow cytometry. Statistics, unless otherwise indicated, was performed by comparing each consecutive treatment with premixed treatment (*P<0.0001, P<0.005, *P<0.05, n.s.: no significant difference). All data are presented as mean±SD (n=3).
Figure 6:
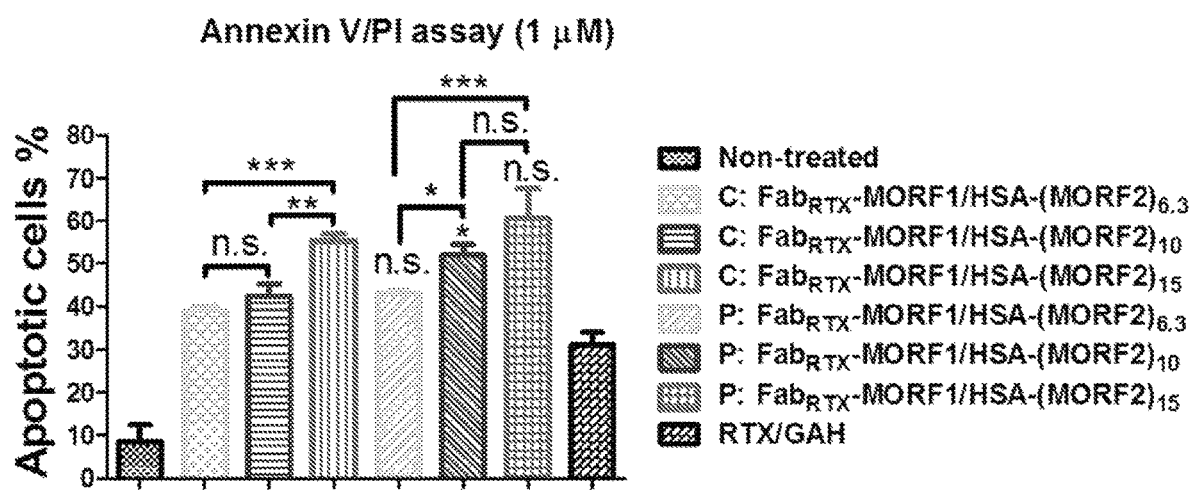
FIG. 6 shows the effect of the degrees of substitution of HSA-(MORF2)x (co-treatment with Fab'$_{RTX}$-MORF1) on apoptosis induction of Raji B-cells. Percentage of apoptotic cells was analyzed by Annexin V/PI binding and quantified by flow cytometry. Incubation time was 24 h. Non-treated, cells in culture medium; RTX/GAM, RTX mAb (0.5 µM) followed (1 h later) by goat anti-mouse secondary Ab (0.25 µM); P: Fab'$_{RTX}$-MORF1/HSA-(MORF2)x, premixture of Fab'$_{RTX}$-MORF1 (1 µM) and HSA-(MORF2)x with different degrees of substitution (HSA-(MORF2)$_{6.3}$ or HSA-(MORF2)$_{10}$ or HSA-(MORF2)$_{14.7}$; 1 µM, MORF2-eqv). C: Fab'$_{RTX}$-MORF1/HSA-(MORF2)x, consecutive, Fab'$_{RTX}$-MORF1 (1 µM) followed (1 h later) by HSA-(MORF2)x with different degrees of substitution (HSA-(MORF2)$_{6.3}$ or HSA-(MORF2)$_{10}$ or HSA-(MORF2)$_{14.7}$; 1 µM, MORF2-eqv). Percentage of apoptotic cells was quantified by flow cytometry. Statistics, unless otherwise indicated, was performed by comparing each consecutive treatment with premixed treatment (*P<0.0001, P<0.005, *P<0.05, n.s.: no significant difference). All data are presented as mean±SD (n=3).

To evaluate the efficacy of HSA-(MORF2)x in apoptosis induction, co-treatments Raji cells with Fab'$_{1F5}$-MORF1 and HSA-(MORF2)x were concerning first. The results of apoptosis induction as determined by Annexin V/PI assay are shown in FIG. 5. Apoptosis studies obtained following co-treatment Raji cells with nanoconjugates Fab'1F5-MORF1 and HSA-(MORF2)x, either as a premixture or consecutively, showed that HSA is serving as an effective protein carrier for morpholino oligonucleotides. The resulting HSA-(MORF2)x, which is using HSA to graft with multiple substitutions of MORF2, has some biorecognition behavior that resembles the function of P-MORF2. HSA-(MORF2)x can ligate Fab'$_{1F5}$-MORF1 via MORF1-MORF2 hybridization at cell surface with concomitant CD20 cross-linking and trigger apoptosis. The substitution degrees-responsive trends were observed in both consecutive and premixed treatment regimens. The impact of degrees of substitution of HSA-(MORF2)x was clearly demonstrated. Increased degrees of substitution of HSA-(MORF2)x resulted in higher levels of apoptosis. All conjugates were more effective than positive control-1F5/GAM.

(c) Evaluation of In Vivo Efficacy in a Murine Model of Human NHL

In vivo therapeutic efficacy of the hybridization-mediated drug-free macromolecular therapeutics was evaluated in SCID (C.B-17) mice bearing systemically disseminated Raji B cells. This animal model has a near 100% tumor engraftment rate, and the hind-limb paralysis-free survival time after treatment accurately reflects anticancer efficacy.

Female C.B-17 SCID mice (Charles River Laboratories, Wilmington, Mass.) at about 7 weeks of age were intravenously injected with 4×10$^6$ Raji-luc cells in 200 µL saline via the tail vein (day 0). This animal model represents dissemination, infiltration and growth of lymphoma cells in various organs, including spinal cord that leads to hind-limb paralysis and subsequent animal death. The onset of hind-limb paralysis was the experimental end point; in addition, mice were sacrificed when body weight loss was >20%. Animals without signs of paralysis/sickness were kept until 100 days and considered long-term survivors. Four groups of animals were evaluated: PBS: Three-dose treatment on days 1, 3 and 5 with phosphate buffered saline (control; n=4); Fab'$_{RTX}$-MORF/HSA-(MORF2)$_{14.7}$: Consecutive treatment with Fab'$_{RTX}$-MORF1 (58 µg/20 g mouse; 1 nmol Fab' equivalent per mouse) and 5 h later of HSA-(MORF2)$_{14.7}$, 3 doses (12.8 µg/20 g mouse; 1 nmol MORF2 per mouse; MORF1: MORF2=1:1) on days 1, 3, and 5 (n=5); Fab'$_{1F5}$-MORF1/HSA-(MORF2)$_{10}$; Consecutive treatment with Fab'1F5-MORF1 and 5 h later of HSA-(MORF2)$_{10}$, 3 doses (1 nM Fab' equivalent per mouse; MORF1:MORF2=1:1) on days 1, 3, and 5 (n=5);

Obinutuzumab:

Single dose of Obitunuzab (75 µg/20 g mouse) on day 1. The paralysis-free survival of mice is presented in a Kaplan-Meier plot. Numbers of long-term survivors in each group are indicated.

Bioluminiscence Imaging.

In vivo imaging was performed at predetermined time intervals. Mice were anesthetized with 2% (v/v) isoflurane gas (IsoFlo®, Abbott Laboratories) in oxygen from a precision vaporizer and intraperitoneally injected with 3 mg firefly D-luciferin (Biosynth). At 15 min post-injection of luciferin (a predetermined time interval, with maximal luciferase signal intensity), mice were scanned at the prone position. Xenogen IVIS® Spectrum (Perkin Elmer) was used, with 1 min exposure time, medium binning, and 1 f/stop. Images were acquired and analyzed under the Living Image® (Perkin Elmer) software environment. Region of interest (ROI) was selected by drawing contours to include the whole mice. Luciferase light unit was quantified in average radiance (photons/sec/cm$^2$/sr). For ex vivo analysis, mice were injected with 3 mg luciferin 12 min prior to being sacrificed. Various organs and tissues (heart, liver, spleen, kidney, lung, intestine, stomach, muscle, brain, spinal cord, femur, tibia, and mesenteric and inguinal lymph nodes) were harvested for imaging. Acquisition parameters were as follows: 1 min exposure time, small binning, and 1 f/stop.

(d) Confocal

Figure 7A:
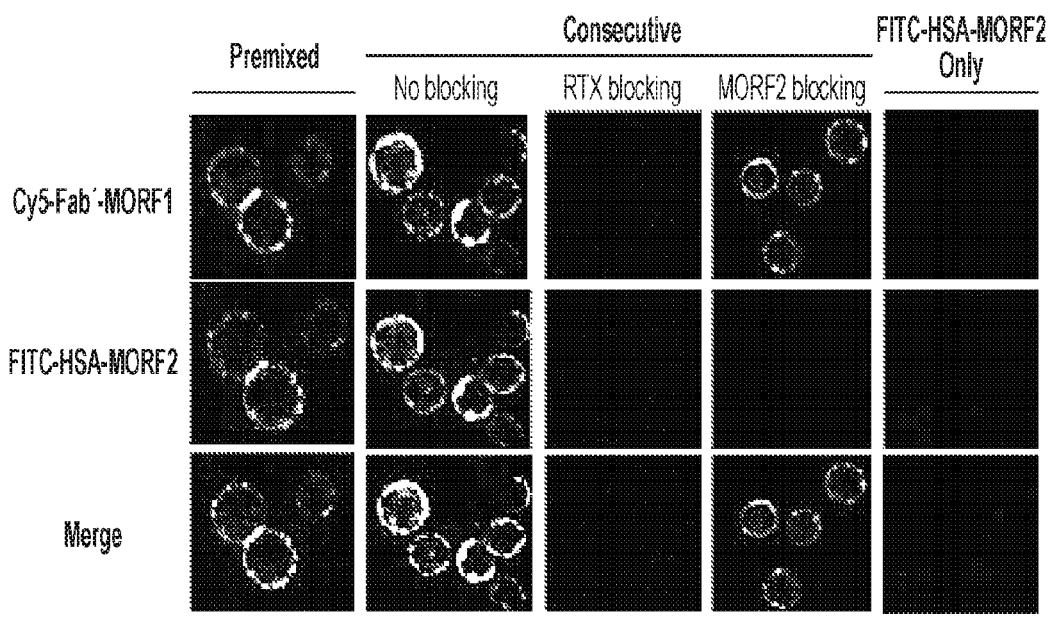
FIGS. 7A, 7B, and 7C show the visualization of colocalization between Cy5-Fab'$_{RTX}$-MORF1 and FITC-HSA-MORF2 on Raji cell surface. (A) Representative confocal images of Raji cells treated with Cy5-Fab'$_{RTX}$-MORF1 and FITC-HSA-MORF2. The Raji lymphoma B cells were incubated with the premixture of two conjugates, or consecutively exposed to Cy5-Fab'-MORF1 and then to FITC-HSA-MORF2. In consecutive treatment, for blocking purpose, excess (100-fold) RTX antibody (Ab) was added prior to Cy5-Fab'$_{RTX}$-MORF1, or excess (100-fold) MORF2 was added prior to FITC-HSA-MORF2. The cells treated with FITC-HSA-MORF2 only (without Cy5-Fab'$_{RTX}$-MORF1) served as a control. Cy5; FITC. Scale bar, 20 µm. (B) and (C) z-stack confocal images of distribution patterns of, Cy5-Fab'$_{RTX}$-MORF1 and FITC-HSA-MORF2 on the Raji cell surface. The Raji cells were (B) incubated with the premixture of two conjugates, or (C) consecutively treated with two conjugates. Graticule size, 10 µm.
Figure 7B:
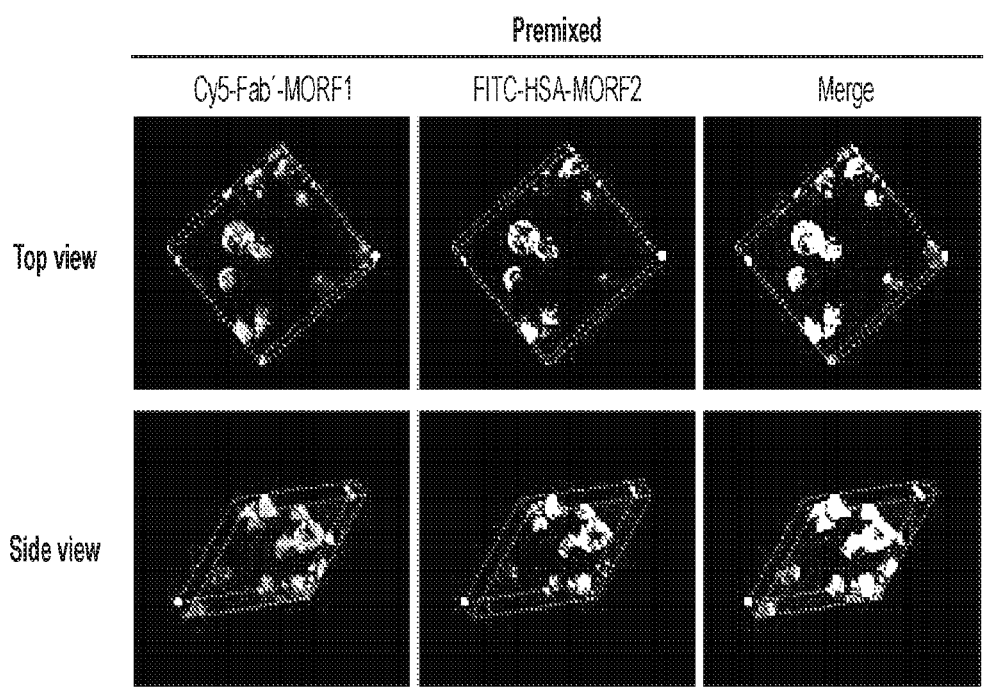
Figure 7C:
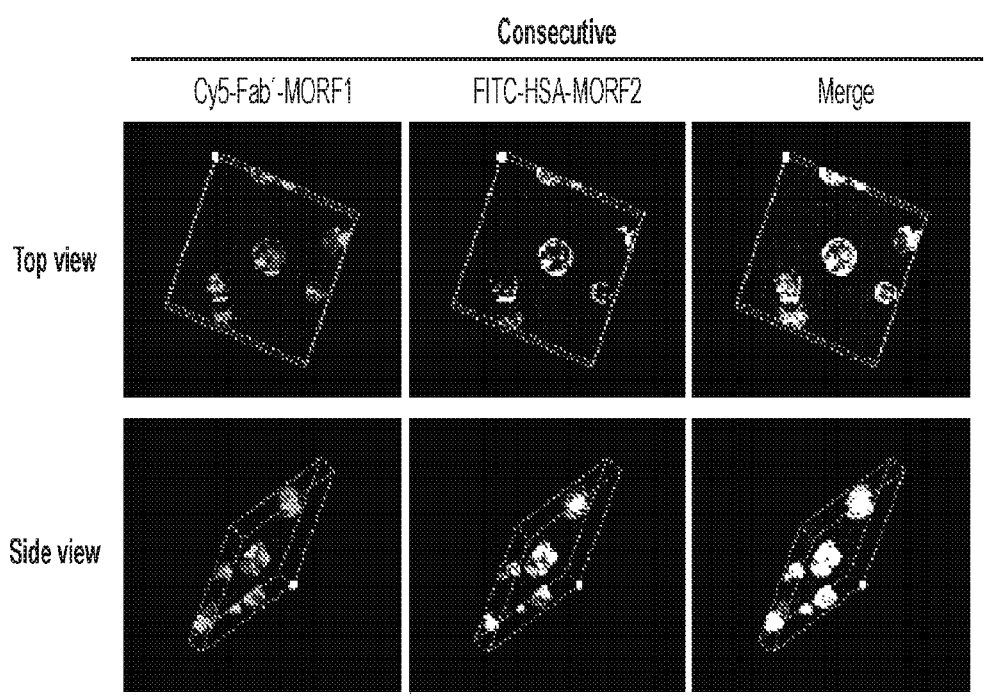

Although previous analysis of the hybridization by UV-visible spectroscopy and hydrodynamic effective diameters by dynamic light scattering showed that Fab-MORF1 and P-MORF2 conjugates, when mixed in solution, self-assembled via MORF1-MORF2 biorecognition, it is necessary to demonstrate that Cy5-Fab'$_{RTX}$-MORF1 and FITC-HSA-MORF2 can also specifically assemble at CD20 antigens on the cell surface. Thus, we conducted in vitro confocal microscopy study, using CD20-expressing human NHL Raji B cell line (FIG. 7). Exposure of Raji cells to the premixture of both fluorescently labeled conjugates (Cy5-Fab'$_{RTX}$-MORF1 and FITC-HSA-MORF2) resulted in well colocalization of Cy5 and FITC signals at the surfaces of B-cells. In the consecutive treatment, when Raji cells were exposed to Cy5-Fab-MORF1 firstly for 1 h and then treated with FITC-HSA-MORF2, the fluorescent images also showed colocalization of two signals. If the cells were pre-blocked with an excess amount of Rituximab before fluorescently labeled conjugates, neither of these two signals can be found. The blocking effect were also performed when the Cy5-Fab'$_{RTX}$-MORF1 conjugates decorated on cell surface were hybridized with normal MORF2 motif ahead, that FITC signal was absent. Cells exposed to only FITC-HSA-MORF2 did not show any fluorescent signal. These microscopic results confirmed that Fab'$_{RTX}$-MORF1 and HSA-MORF2 conjugates could assemble on cell surface through effective MORF1-MORF2 hybridization.

REFERENCES

1. T.-W. Chu, R. Zhang, J. Yang, M. P. Chao, P. Shami, J. Kopeček, A two-step pretargeted nanotherapy for CD20 crosslinking may achieve superior anti-lymphoma efficacy to rituximab. Theranostics 5, 834-846 (2015).
2. K. Wu, J. Liu, R. N. Johnson, J. Yang, J. Kopeček, Drug-free macromolecular therapeutics: Induction of apoptosis by coiled-coil mediated crosslinking of antigens on cell Surface. Angew. Chem. Int. Ed. 49, 1451-1455 (2010).
3. T.-W. Chu, J. Yang, R. Zhang, M. Sima, J. Kopeček, Cell surface self-assembly of hybrid nanoconjugates via oligonucleotide hybridization induces apoptosis. ACS Nano 8, 719-730 (2014).
4. T.-W. Chu, K. M. Kosak, P. J. Shami, J. Kopeček, Drug-free macromolecular therapeutics induce apoptosis of patient chronic lymphocytic leukemia cells. Drug Delivery Translational Res. 4, 389-394 (2014).
5. G. Liu, G. Mardirossian, J. He, S. Zhang, X. Liu, M. Rusckowski, D. J. Hnatowich, Successful radiotherapy of tumor in pretargeted mice by 188Re-radiolabeled phosphorodiamidate morpholino oligomer, a synthetic DNA analogue. Clin. Cancer Res. 12, 4958-4964 (2006).
6. J. J. Mulvey, C. H. Villa, M. R. McDevitt, F. E. Escorcia, E. Casey, D. A. Scheinberg, Self-assembly of carbon nanotubes and antibodies on tumours for targeted, amplified delivery. Nat. Nanotechnol. 8, 763-771 (2013).
7. J. Gunn, S. I. Park, O. Veiseh, O. W. Press, M. Zhang, A pretargeted nanoparticle system for tumor cell labeling. Mol. Biosyst. 7, 742-748 (2011).
8. T.-W. Chu, J. Kopeček, Drug-free macromolecular therapeutics—a new paradigm in polymeric nanomedicines. Biomaterials Sci. 3, 908-922 (2015).
9. R. L. Siegel, K. D. Miller, A. Jemal, Cancer statistics, 2015. CA Cancer J. Clin. 65, 5-29 (2015).
10. K. R. Shankland, J. O. Armitage, B. W. Hancock, Non-Hodgkin lymphoma. Lancet 380, 848-857 (2012).
11. J. O. Armitage, D. D. Weisenburger, New approach to classifying non-Hodgkin's lymphomas: clinical features of the major histologic subtypes. Non-Hodgkin's lymphoma classification project, J. Clin. Oncol., 16, 2780-2795 (1998).
12. A. D. Zelenetz, L. I. Gordon, W. G. Wierda, J. S. Abramson, R. H. Advan, C. B. Andreadis, N. Bartlett, J. C. Byrd, M. S. Czuczman, L. E. Fayad, R. I. Fisher, M. J. Glenn, N. L. Harris, R. T. Hoppe, S. M. Horwitz, C. R. Kelsey, Y. H. Kim, S. Krivacic, A. S. LaCasce, A. Nademanee, P. Porcu, O. Press, R. Rabinovitch, N. Reddy, E. Reid, A. A. Saad, L. Sokol, L. J. Swinnen, C. Tsien, J. M. Vose, J. Yahalom, N. Zafar, M. Dwyer, H. Sundar, Non-Hodgkin's lymphomas, version 4.2014. J. Natl. Compr. Cancer Netw. 12, 1282-1303 (2014).
13. D. G. Maloney, A. J. Grillo-López, C. A. White, D. Bodkin, R. J. Schilder, J. A. Neidhart, N. Janakiraman, K. A. Foon, T. M. Liles, B. K. Dallaire, K. Wey, I. Royston, T. Davis, R, Levy, IDEC-C2B8 (Rituximab) anti-CD20 monoclonal antibody therapy in patients with relapsed low-grade non-Hodgkin's lymphoma. Blood 90, 2188-2195 (1997).
14. D. G. Maloney, Anti-CD20 antibody therapy for B-cell lymphomas, N. Engl. J. Med. 366, 2008-2016 (2012).
15. A. Molina, A decade of rituximab: improving survival outcomes in non-Hodgkin's lymphoma, Annu. Rev. Med. 59, 237-250 (2008).
16. G. Cartron, L. Dacheux, G. Salles, P. Solal-Celigny, P. Bardos, P. Colombat, H. Watier, Therapeutic activity of humanized anti-CD20 monoclonal antibody and polymorphism in IgG Fc receptor FcγRIIIa gene. Blood 99, 754-758 (2002).
17. M. R. Smith, Rituximab (monoclonal anti-CD20 antibody): mechanisms of action and resistance. Oncogene 22, 7359 (2003).
18. I. Dransfield, Inhibitory FcγRIIb and CD20 internalization. Blood 123, 606-607 (2014).
19. T. Pham, P. Mero, J. W. Booth, Dynamics of macrophage trogocytosis of rituximab-coated B cells. PloS One 6, e14498 (2011).
20. P. Stashenko, L. M. Nadler, R. Hardy, S. F. Schlossman, Characterization of a human B lymphocyte-specific antigen. J. Immunol. 125, 1678-1685 (1980).
21. K. C. Anderson, M. P. Bates, B. L. Slaughenhoupt, G. S. Pinkus, S. F. Schlossman, L. M. Nader Expression of human B cell-associated antigens on leukemias and lymphomas: a model of human B cell differentiation. Blood 63, 1424-1433 (1984).
22. O. W. Press, A. G. Farr, K. I. Borroz, S. K. Anderson, P. J. Martin, Endocytosis and degradation of monoclonal antibodies targeting human B-cell malignancies. Cancer Res. 49, 4906-4912 (1989).
23. R. B. Michel, M. J. Mattes, Intracellular accumulation of the anti-CD20 antibody 1F5 in B-lymphoma cells. Clin. Cancer Res. 8, 2701-2713 (2002).
24. J. K. Bubien, L. J. Zhou, P. D. Bell, R. A. Frizzell, T. F. Tedder, Transfection of the CD20 cell surface molecule into ectopic cell types generates a Ca2+ conductance found constitutively in B lymphocytes. J. Cell Biol. 121, 1121-1132 (1993).
25. T. F. Tedder, P. Engel, CD20: a regulator of cell-cycle progression of B lymphocytes, Immunol. Today 15, 450-454 (1994).
26. E. Janas, R. Priest, R. Malhotra, Functional role of lipid rafts in CD20 activity?Biochem. Soc. Symp., 2005, 165-175.
27. B. D. Cheson, J. P. Leonard, Monoclonal antibody therapy for B-cell non-Hodgkin's lymphoma. N. Engl. J. Med. 359, 613-626 (2008).
28. P. Boross, J. H. W. Leusen, Mechanisms of action of CD20 antibodies. Am. J. Cancer Res. 2012, 2, 676-690 (2012).
29. M. Okroj, A. Osterborg, A. M. Blom, Effector mechanisms of anti-CD20 monoclonal antibodies in B cell malignancies. Cancer Treat. Rev. 39, 632-639 (2013).
30. D. Shan, J. A. Ledbetter, O. W. Press, Apoptosis of malignant human B cells by ligation of CD20 with monoclonal antibodies. Blood 91, 1644-1652 (1998).
31. J. M. Hartley, T.-W. Chu, E. M. Peterson, R. Zhang, J. Yang, J. Harris, J. Kopeček, Super-resolution imaging and quatitative analysis of membrane protein/lipid raft clustering mediated by cell surface self-assembly of hybrid nanoconjugates. ChemBioChem 16, 1725-1729 (2015).
32. R Zhang, J Yang, T-W Chu, J M Hartley, J Kopeček, Multimodality imaging of coiled-coil mediated self-assembly in a "drug-free" therapeutic system. Adv. Healthc. Mater. 4, 1054-1065 (2015).

33. J. Kopeček, J. Yang, T.-W. Chu T-Compositions and methods for inducing apoptosis. US Patent Application, PCT/US2014/023784, filed: Mar. 11, 2014.
34. M. Bern, K. M. Knutsen Sand, J. Nilsen, I. Sandlie, J. T. Andersen, The role of albumin receptors in regulation of albumin homeostasis: Implications for drug delivery. J. Controlled Release 211, 144-152 (2015).
35. F. Kratz, Albumin as a drug carrier: Design of prodrugs, drug conjugates and nanoparticles. J. Controlled Release 132, 171-183 (2008).
36. J. T. Andersen, B. Dalhus, D. Viuff, B. T. Ravn, K. S. Gunnarsen, A. Plumridge, K. Bunting, F. Antunes, R. Williamson, S. Athwall, E. Allan, L. Evans, M Bjoras, S. Kjaerulff, D. Sleep. I. Sandlie, J. Cameron, Extending serum half-life of albumin by engineering neonatal Fc receptor (FcRn) binding. J. Biol. Chem. 289, 13493-13502 (2014).
37. A. Sethi, M. Sher, M. R. Akram, S. Karim, S. Khiljee, A. Sajjad, N. H. Shah, G. Murtaza, Albumin as a drug delivery and diagnostic tool and its market approved products. Acta Pol. Pharmaceutics—Drug Res. 70, 597-600 (2013).
38. B. Elsadek, F. Katz, Impact of albumin on drug delivery—New applications on the horizon. J. Controlled Release 157, 4-28 (2012).
39. N. Desai, V. Trieu, B. Damascelli, P. Soon-Shiong, SPARC expression correlates with tumor response to albumin-bound paclitaxel in head and neck cancer patients. Transl. Oncol. 2, 59-64 (2009).
40. G. Liu, J. He, S. Dou, S. Gupta, J. L. Vanderheyden, M. Rusckowski, D. J. Hnatowich, Pretargeting in tumored mice with radiolabeled morpholino oligomer showing low kidney uptake. Eur. J. Nucl. Med. Mol. Imaging 31, 417-424 (2004).
41. A. M. Ghetie, J. Richardson, T. Tucker, D. Jones, J. W. Uhr, E. S. Vitetta, Disseminated or localized growth of a human B-cell tumor (Daudi) in SCID mice. Int. J. Cancer 45, 481-485 (1990).
42. A. M. Ghetie, K. Tucker, J. Richardson, J. W. Uhr, E. S. Vitetta, The Antitumor activity of an anti-CD22 immunotoxin in SCID mice with disseminated Daudi lymphoma is enhanced by either an anti-CD19 antibody or an anti-CD19 immunotoxin. Blood 80, 2315-2320 (1992).
43. G. L. Griffiths, M. J. Mattes, R. Stein, S. V. Govindan, I. D. Horak, H. J. Hansen, D. M. Goldenberg, Cure of SCID mice bearing human B-lymphoma xenografts by an anti-CD74 antibody-anthracycline drug conjugate. Clin. Cancer Res. 9, 6567-6571 (2003).

---

What is claimed is:

1. A method of inducing apoptosis, the method comprising:
   (i) contacting a population of cells comprising CD20 positive cells with a first conjugate comprising a targeting moiety and a morpholino, wherein the targeting moiety is an anti-CD20 antibody or an anti-CD20 Fab' fragment; and
   (ii) contacting the population of cells with a second conjugate comprising albumin and one or more morpholinos;
   wherein the morpholino of the first conjugate is 5' GAG TAA GCC AAG GAG AAT CAA TAT A 3' (SEQ ID NO:25) or 5' TAT ATT GAT TCT CCT TGG CTT ACT C 3' (SEQ ID NO:26) and wherein the one or more morpholinos of the second conjugate are 5' GAG TAA GCC AAG GAG AAT CAA TAT A 3' (SEQ ID NO:25) or 5' TAT ATT GAT TCT CCT TGG CTT ACT C 3' (SEQ ID NO:26), wherein the morpholino of the first conjugate and the one or more morpholinos of the second conjugate are complementary,
   wherein the contacting of the cells with the first conjugate and the second conjugate induces apoptosis of the CD20 positive cells.

2. The method of claim 1, further comprising repeating step (i) and step (ii).

3. The method of claim 1, further comprising (iii) confirming apoptosis of the cells.

4. The method of claim 1, wherein the CD20 positive cells are B cells.

5. The method of claim 1, wherein the cells are in a subject.

6. The method of claim 5, wherein the subject has non-Hodgkin's lymphoma or rheumatoid arthritis.

7. The method of claim 1, wherein the anti-CD20 receptor antibody is 1F5, rituximab, tositumomab, ibritumomab, ofatumumab, veltuzumab ocrelizumab, ocaratuzumab, obinutuzumab, PRO131921, BCD-020, IBI-301, ublituximab, or BLX-301.

8. The method of claim 1, wherein the albumin is human serum albumin.

9. A method of inducing apoptosis, the method comprising:
   contacting a population of cells comprising CD20 positive cells with a composition comprising
   a first conjugate comprising a targeting moiety and a morpholino, wherein the targeting moiety is an anti-CD20 antibody or an anti-CD20 Fab' fragment and
   a second conjugate comprising a conjugate comprising albumin and one or more morpholinos,
   wherein the morpholino of the first conjugate is 5' GAG TAA GCC AAG GAG AAT CAA TAT A 3' (SEQ ID NO:25) or 5' TAT ATT GAT TCT CCT TGG CTT ACT C 3' (SEQ ID NO:26) and wherein the one or more morpholinos of the second conjugate are 5' GAG TAA GCC AAG GAG AAT CAA TAT A 3' (SEQ ID NO:25) or 5' TAT ATT GAT TCT CCT TGG CTT ACT C 3' (SEQ ID NO:26), wherein the morpholino of the first conjugate and the one or more morpholinos of the second conjugate are complementary,
   wherein the contacting of the cells with the composition induces apoptosis of the CD20 positive cells.

10. A kit comprising (i) a first conjugate comprising a targeting moiety and a morpholino, wherein the targeting moiety is an anti-CD20 antibody or an anti-CD20 Fab' fragment and (ii) a second conjugate comprising albumin and one or more morpholinos,
    wherein the morpholino of the first conjugate is 5' GAG TAA GCC AAG GAG AAT CAA TAT A 3' (SEQ ID NO:25) or 5' TAT ATT GAT TCT CCT TGG CTT ACT C 3' (SEQ ID NO:26) and wherein the one or more morpholinos of the second conjugate are 5' GAG TAA GCC AAG GAG AAT CAA TAT A 3' (SEQ ID NO:25) or 5' TAT ATT GAT TCT CCT TGG CTT ACT C 3' (SEQ ID NO:26), wherein the morpholino of the first conjugate and the one or more morpholinos of the second conjugate are complementary.

11. The method of claim 9, further comprising confirming apoptosis of the cells.

12. The method of claim 9, wherein the CD20 positive cells are B cells.

13. The method of claim 9, wherein the cells are in a subject.

14. The method of claim 13, wherein the subject has non-Hodgkin's lymphoma or rheumatoid arthritis.

15. The method of claim 9, wherein the anti-CD20 receptor antibody is 1F5, rituximab, tositumomab, ibritumomab, ofatumumab, veltuzumab ocrelizumab, ocaratuzumab, obinutuzumab, PRO131921, BCD-020, IBI-301, ublituximab, or BLX-301.

16. The method of claim 9, wherein the albumin is human serum albumin.

* * * * *